US008911939B2

(12) United States Patent
Kaufman et al.

(10) Patent No.: US 8,911,939 B2
(45) Date of Patent: Dec. 16, 2014

(54) DETECTION OF JOHNSONGRASS AND ITS HYBRID SEED

(75) Inventors: Benjamin Kaufman, West Des Moines, IA (US); Mulu Ayele, Johnston, IA (US); Olga Ellern, Ames, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 554 days.

(21) Appl. No.: 13/093,956

(22) Filed: Apr. 26, 2011

(65) Prior Publication Data

US 2011/0269639 A1 Nov. 3, 2011

Related U.S. Application Data

(60) Provisional application No. 61/329,271, filed on Apr. 29, 2010.

(51) Int. Cl.
*C12Q 1/68* (2006.01)

(52) U.S. Cl.
CPC .................................. *C12Q 1/6895* (2013.01)
USPC ........................................................ 435/6.1

(58) Field of Classification Search
None
See application file for complete search history.

(56) References Cited

U.S. PATENT DOCUMENTS

2009/0081646 A1 * 3/2009 Taberlet et al. ................... 435/6

FOREIGN PATENT DOCUMENTS

WO 00/40695 * 7/2000

OTHER PUBLICATIONS

Chen Qin et al. (Not. Bot. Hort. Agrobot. Cluj 36 (1) 2008, 55-58).*
GenBank Accession AI724294. Jul. 19, 2000, two pages.*
Jang et al. Plant physiology (Nov. 2006) 142:1148-1159.*
Ha et al. (Gene 386 (2007) 115-122).*
Jang, et al.; "Functional Classification, Genomic Organization, Putatively cis-Acting Regulatory Elements, and Relationship to Quantitative Trait Loci, of Sorghum Genes with Rhizome-Enriched Expression"; Plant Physiology (Nov. 2006) 142:1148-1159; American Society of Plant Biologists; Rockville, MD US.
Cordonnier-Pratt, et al.; Gen Bank Accession No. A1724294.1; Sorghum halepense cDNA, mRNA sequence; 2000.

* cited by examiner

*Primary Examiner* — Juliet Switzer
(74) *Attorney, Agent, or Firm* — Pioneer Hi-Bred Int'l, Inc.

(57) ABSTRACT

Methods for detecting the presence or amount of Johnsongrass or Johnsongrass hybrid genetic material in a biological sample, preferably the detection of the presence or amount of Johnsongrass or Johnsongrass hybrid seed in a seed sample, are disclosed. The methods involve detection of certain nucleic acid sequences, namely Johnsongrass detection sequences, optionally through a primer-based amplification process, such as PCR. Also disclosed are isolated polynucleotides, replication compositions and kits for carrying out the detection methods.

2 Claims, No Drawings

ABSTRACT

SEQUENCE LISTING

<160> NUMBER OF SEQ ID NOS: 140

<210> SEQ ID NO 1
<211> LENGTH: 969
<212> TYPE: DNA
<213> ORGANISM: Sorghum halepense

<400> SEQUENCE: 1

```
tttttttttt ttttttttgt ttggaatctg gctttcattt tgggaatgag gcaaatcaag      60
ccattggttc ctgatacatt tttagctaat aaatgaaact tcaactcacc atacatgcac     120
ttgtacatat tcattctact gcttgcacta cgtacaacat ttgagcaaca gcagagagat     180
gctcaacctc tcgctctttc tttattaatt gaacgtgctt cttatatgat cctcaccaca     240
gaatacattt atatttatcc acctcttcct tggctttaac aggaatcgtt agtagtttat     300
ttcattcttt cattcagaat gggggtcac cgtatcaaaa tatcaaattc tctgagaagg     360
gcgaccgcca tggagaattc cagggtgtag ccaaacagat cagagcctgg agagcttgag     420
ctgctgcttg agcaagggcc ggaggtactc atggtacccc tcaggcacca ccgtctcgtt     480
caaagggtcc ttccacgcct cctcatacag tgccgggtac acattcccgt cataccgccc     540
cagcaccgac cccaggtagt ggtctgtgta gttgaacgca tccaccagag caacagcatt     600
tggacgcacc tgtgcgtaaa gtttgccaag ttgctcattt gccaacgctc cctgcttcgg     660
tgtgatgcac ccagttgcca ggaagtcgcc caggtgcttg tgaagaatgt agagggcata     720
aacattgcaa aggttctggc tcgtgccgaa ttcggcacga gcttctattg aagggagtat     780
ggcaaaagca ctgatgtttc caacaagaac tcatctgaga ttttgttttt tggtctgaat     840
agagtgcttt gttaagattg tggaacgtgt tgtgtgcttc agaaattgag aaccctgtta     900
tgagctatcc ctgcagttaa ttattatgac ctaaaaaaaa aaaaaaaaa aaactcaaga     960
ctagttctc                                                            969
```

<210> SEQ ID NO 2
<211> LENGTH: 836
<212> TYPE: DNA
<213> ORGANISM: Sorghum halepense

<400> SEQUENCE: 2

```
gcacgaggag acctttgagc aagcttgctt gctttgaggg tcagaggggg ctttcggcgc      60
cggccaacca tggggaggt gaagcacctg tgcctggtga agttcaagga gggcgtcgtg     120
gtggaggatg tcctcaaagg catgactgac ctcgtggccg ggatggacat ggtgaaatct     180
ttcgagtggg gtcaggacgt gctgaaccag gagatgctga cgcagggctt cacccacgtc     240
ttctcgctga ccttcgcctc cgccgacgac ctggccacct acatgggcca cgacaggcac     300
gccgcgttcg ccgccacctt catggccgcg ctcgacaagg tggtcgtcat cgacttcccc     360
gtcgtcgtcg ccaagccgcc gcctccggca tgatctgccg ccggccattg tatcgtacgg     420
cgcccttttt caggtagcat cagatcagat ccatgtgtgt tgcagcgctg ctgctgctgg     480
tgtgctactg cttactgtac gtacttagtg gtactactat ttattgcttg ttctgctcta     540
tctatctatc tatctatcta tctatatata tctataatat gtccccggtt agtgcatgca     600
```

-continued

```
tggtgtagta gctgtaagcc tgtaaactct gcaaggcaaa aatatctgca ccgtgcactc    660
tccgttcaag tacctattgt ttggttatct ttggaataaa ttccggtcac ctttctggta    720
gcatatatat agccagctag tagctgcttg taatctgtct ctcgtttctt ttcggtgttt    780
tatgatggat tgacagattc ctcctaaaaa aaaaaaaaaa aaaaaaaaaa aaaaaa        836
```

<210> SEQ ID NO 3
<211> LENGTH: 775
<212> TYPE: DNA
<213> ORGANISM: Sorghum halepense

<400> SEQUENCE: 3

```
ttttttttt tttttttttt ttttacacaa agacggggga tattataggt aatagatgga     60
tggtgacaca gcacaaacaa aagtcacaca cgatcgacgt gcccacagag caggggggcat  120 gcacggcctg ctgctgtgct gcactgcacc cacaaacaca caacacaaca ccgactgcta   180
gtagatgagc ccccggagga gcacgggaag gacgacagga cgacacgacg ccaacatccc   240
agtacaatta ttattggttc ccatcagtac cagaaccact agcatatggt gccatggcac   300
tcgactgact ggctgactca aacacacaca cacacacaca cactgcagtg acgacactgc   360
tagctatact agctaaggga atctgtcctt cctccgggct gcagtgcagt gcagggggtt   420
attatacagc tcacttgcag gtgcaggggt tgcagctgca gttggggccg cacttgcacc   480
cgtcgttctc agctccggcg ccggccgccg cctcgaaccc gccctcggcg tgccccttgg   540
acgatggtgc gacacccatg acgacagtct tggtggtggt ggtggtcacc tgctcagcca   600
tgtccgggta catcttgcac cctccgcagc cgctgccgca cttgcagccg gagccgcacc   660
cgcagttgcc tccgcagcac gacatcctcc aaaggaactg atggaatgga atgaagctcg   720
ccaataatca aacgatcagg atcgagatag attatgcaat taatcttcgc cctgc         775
```

<210> SEQ ID NO 4
<211> LENGTH: 591
<212> TYPE: DNA
<213> ORGANISM: Sorghum halepense

<400> SEQUENCE: 4

```
gcacgagaaa ggggctaaga tcatatcata atctttgtat gacaaaagca gggatcctct     60
tcaaaatgat gagatcaaac aaaacatgtt tcgatggaat ttcaagaaag cttgacacag    120
tcgattctgt ctcgtgccga attcggcacg agcccaaggc tgcgctcgtc aacgaccgcc    180
cccatgttaa ggcgtggtgg gaggagatcg ccaagcgccc cgcgttccag aagaccgtcg    240
ccgccatccc attcccaccg ccgccctcct ccgcttgagt tgacctttcg ctgggtcgtc    300
gccggtcacg gacgcctccg agttgaataa aaacggcctc cttgcttgtt gctgcgccgt    360
tgtgtgaatc aaatccaaat caaataaata ctgtactgta gttgttttca tgtgtgttca    420
tctcactgct gtctcggctt ggttgtgtga agagcacggt gggggtgtgg acacgatgtg    480
tagaaccttt ttttttttga tccttggatg tttctattag ccagttgctt aatcttatca    540
gctgaatctg gtgttttct ctatcaataa atctgctacg gcttattagg c              591
```

<210> SEQ ID NO 5
<211> LENGTH: 660
<212> TYPE: DNA
<213> ORGANISM: Sorghum halepense

<400> SEQUENCE: 5

```
caaactcaga agttagctag ctccgctctt acactccaag cagcagcgaa gtagctagtg      60
ttgttggcaa caaagcggta gatctcgcga ggtcgagaag atgaagagca gcactctctt     120
gacgatccta gtgctccagg cccttctggt ctctgcagct atggccaaag acaagggcc      180 gaagaaggcg tgctgcaaag agtgcaccag ctggtcgggt gtgtacacct gcgacgacct     240
cctgaccaag tgcgccgcca cctgcaagca atgcgtcccc gtgtccacgg acaagggcac     300
ccgctacagg tgccgcgact tcctccccga aggctgcccc tgcaagacca actgatccat     360
ccatccatcc acaccacgca tgcatggcca cagccgatgg atctacatat gctccgtccg     420
ccttatatac tactatatat aaggcgccaa taataaagat tgttgttgtc ttgcttgttt     480
ggatgatgtc ccttctccat cgagatggaa taaaataaag tcaggcgcac tgatatggtg     540
tgttaattaa gcatatttat tatcttctgt aaaccagtat atatcgacca tgcttacact     600
acgatacatg ctcatgaaaa caaccaaaag acaataaacc ctcctgtccc ggtattgatc     660

<210> SEQ ID NO 6
<211> LENGTH: 630
<212> TYPE: DNA
<213> ORGANISM: Sorghum halepense

<400> SEQUENCE: 6
cattgatggg tcctacgatc aacctgtacg gcgccactga gtctgggcag cggactcgtt      60
gcgtggagcg tctggaggag gccggcgccg attaccgaat cctgccccta cttctcgacc     120
ccgcccatca ctatagcccc caacacctcc ccacccccc gatccgtcaa cttccacctt     180
tccgatatgg ttatctcttc ctatggtaat catctgcact tttcgaaatc gttggtcgtt     240
tgaacaaggc ttacttgctg aagcaaggca acctccctga gtcaaccctg ccgcacgtat     300
gcctggatgt ggaatccgtc catggcaccg ccgccctgac cctctcctg caccattgcc     360 tctatccccc tctattccgt cgccccacct atcataaggt gctccacgaa aacctgaata     420
atctaagaaa agcgctagaa gtgtacgaag gtcgtctcgg cgagcacagc taccttcccc     480
gagacttcct ccctctcccc aacctccctc acctctccct acctctatca ctgctcccta     540
cccctcatgc tgctctgctc aacgcatact ctcacgttca ggcctgacgc tatggtctca     600
tggtcatgcc atctgttcat aacgtcgccg                                     630

<210> SEQ ID NO 7
<211> LENGTH: 104
<212> TYPE: DNA
<213> ORGANISM: Sorghum halepense

<400> SEQUENCE: 7
tttttttttt tttttttttt tcccacattt ttttaataa aattttaaat aacgataaaa      60
catgattcca aatacatcgg ttaattttat tattcaacac ccga                      104

<210> SEQ ID NO 8
<211> LENGTH: 116
<212> TYPE: DNA
<213> ORGANISM: Sorghum halepense

<400> SEQUENCE: 8
cttataaagc cgacttgcgg gatttcctag atgagccgcc ccatcccgcg ggagtcgagc      60
aagaagacgg gtgacttgcc tggggtccat tgagactgat ggtgtctttt ttcgcg        116

<210> SEQ ID NO 9
<211> LENGTH: 343
```

<212> TYPE: DNA
<213> ORGANISM: Sorghum halepense

<400> SEQUENCE: 9

```
aaagttccct ttatggtcct ctcgttcagg aagttcattg ggtgaatcac aaagtcagca    60
tccttgtcag tctctcccct ttccccagca actcccagc gatagtgcac acattctatt   120
ccttggacca caccattgtt gtgtccattg cattgcgcga tgtggtctac ccctccgttg   180
gtcatctcag caagtccctc ctgcacgcgc ttcttgcgct cttttggctt cagcaatacc   240
gtccaaccag acatcctagc ttcgtgagat ctctttggct tcaggtcatc tcctatgagt   300
cctggataca ccgacagaca gagcgcgaga gagagagaca gag                     343
```

<210> SEQ ID NO 10
<211> LENGTH: 244
<212> TYPE: DNA
<213> ORGANISM: Sorghum halepense

<400> SEQUENCE: 10

```
ctaacctcac cgctttaggg tattttaatt tcggggaggg gtcgtttcct ccccaagcgg    60
ggggtggggg ggaccaaaac cccccccttt ccccccccca cccccctggc cccctttttc   120
tcggaaaata ttttttcttt tttggccccc cccccccgcg agaaaaaaaa cccacacatt   180
tttttctct ctcccgctgg gcgggccaca cccccccact ttggtgggaa aaacaagaa   240
gaaa                                                                244
```

<210> SEQ ID NO 11
<211> LENGTH: 161
<212> TYPE: DNA
<213> ORGANISM: Sorghum halepense

<400> SEQUENCE: 11

```
ggggagtgcg ttcagaggtt caatgatgag gaggtcaagc tggaggaatc tgattcgaag    60
cgagaagccc tatgaaagcg ccttggagga atggctgcc tcaaaacctg gtgaaaacaa   120
tcccttaggt gcacccaatg gcaaacccag tcaagctgct g                       161
```

<210> SEQ ID NO 12
<211> LENGTH: 1068
<212> TYPE: DNA
<213> ORGANISM: Sorghum halepense
<220> FEATURE:
<221> NAME/KEY: misc_feature
<222> LOCATION: (1)..(1068)
<223> OTHER INFORMATION: n=a, c, t, or g

<400> SEQUENCE: 12

```
tctgatttag gtttcttatt ttttgtaatt aaaacaataa aaggactnac tgactggatt    60
accacagtct ctaacaagac acaacgatat taatgagacg tggcagtggt accaatacaa   120
acgtcaacaa tatcaacatt gctcgcaagt taccgaaccc agatactatg cgcaacgcgt   180
gcacatgcgg taaaaaccat ngataataag aaaaatcgta gactcaaaag aacatgtgca   240
gaatcacata tacgataaga taagtctaac agaggaggtc acacacatgt ggagcgtaca   300
attctcnata cgcgccttag cgacaaggna ccgctctttg ctcaacgcca cagttaccaa   360
aggcctatat tgcctcccac agctaacgac agcaacatag cgcgatctgg cagcccgatt   420
tgctatcgtc gcctgccaca ctctcgttgg cggcttatat ccgagaacat gtttggcgtg   480
atgtactaat cgatcttgga tatatccagt tcaaaacacg cgtaacacgt aagtaacatg   540
```

| | |
|---|---:|
| cgcaagagtg agtccgcctc cgaatgtgtt ngctacgcgc atctattact taggcgcatc | 600 |
| ttagatgcaa ttggaacaag tacgacgcta cgagtttcgc actagctacn gaaaatgtgt | 660 |
| tatgccatag atgtgaaatt ccatggcaaa atctcgccgt cgccatggcg ttgtcgtatc | 720 |
| gtgcctacta gccgagtgac atgtcatggt atctcgttcg acctcgagaa tcgacagtcg | 780 |
| tatttcgtag cactcggagc ctatatattc gagaaactgg tcactgagtc cagtacagaa | 840 |
| aaccccgtca atttcactat actaggagtc tcgtactgag ggacattcac cattcgtagg | 900 |
| ggcttctacg aatgcaggag attacaaaaa agaaatctga acaatttccc caggaatttt | 960 |
| gtccagaaaa ttgctgcccg ggaaaacttg cattaaattc cagaatcgtt accccgcca | 1020 |
| ccccggaaaa aagagctggg atataaatgg ctcccgcaaa tatggggc | 1068 |

<210> SEQ ID NO 13
<211> LENGTH: 609
<212> TYPE: DNA
<213> ORGANISM: Sorghum halepense

<400> SEQUENCE: 13

| | |
|---|---:|
| ttggactcac cgcgggcacg ctctagaact atgatccatt gttttccttg atacattcag | 60 |
| cactaacaat gatgttctgt tctgttttg atctttcat gaaccttgtt gtgtcataat | 120 |
| ctttcaggat cttgaatgat gaaggcaatg gagattgttg atgagaatga tcacacatcg | 180 |
| aatctacacg agaacttgaa ctctttataa cacctatacg atcattttcc ctctgagcta | 240 |
| gcttctggga ttgagttagg ctcatcaaca ggcgtcttat tatgtccggt gccacgatgt | 300 |
| gtaaagtccc gaatgcatcg aagacgtaat aaaatgatca atgtctaata agttcatttc | 360 |
| atttaacatt ttttgctcaa atcttttgaa gttttgaaag acaagtttgg tataatccat | 420 |
| gtttatttgt ctttctttt tatatatgag atttgttttt gttttggaga tttgatggta | 480 |
| tgtctgttat ataagataac aatatcactg ttatccattg atgaggtctg gctaaaagta | 540 |
| agcgtgtatg cagactttat ttctacctgg aggtctccga ctacgctgat atctcagatc | 600 |
| ctttgtcaa | 609 |

<210> SEQ ID NO 14
<211> LENGTH: 727
<212> TYPE: DNA
<213> ORGANISM: Sorghum halepense

<400> SEQUENCE: 14

| | |
|---|---:|
| acaccaaagc ggagaagcgg ccaagagatc agcatcaacc acgtctagtt gataacagac | 60 |
| gtgatgggac aattcgtatt tgctaccgga gtccgtacgg tatacactaa aaacacatgg | 120 |
| agtagtttac tctaacgact agggtcgatc ggtggacatg atagcctatc actttgccag | 180 |
| ggcagtagtt gcacagcgtc tgtatcaagc tcaggcctag tatgaagtaa tgcttgtctc | 240 |
| agaagtcctc ctctggggtg tgtcctcgca gctgcgggcg gcaccttaat tagttcacaa | 300 |
| tggatattgc gtctacttac atacaatatt acaggcaact tggagacgaa acccttttgtc | 360 |
| attggttttg cgtatcgtgt ctgatcctcc gaatctaatg ggcctgaaca aaaggcggcc | 420 |
| gctcggtagt gctcgcacgg agtgcccttg gttaaagacg tcggtctct cgaattggac | 480 |
| accagtggcg ttactacact aagagttgcc cgttcttcgc tcatcgtaca ggtattcttt | 540 |
| cttgttcgtg cgtgcgatgt aagttaggtc cttcccgtgc aaaccgttgg aagatacata | 600 |
| gaaagtgcct ggccaggctg ggggttgatc gtttggcctt ccgccacggg gaggcgtcct | 660 |
| cacgctcgcc caaggtttgg actacacaaa acccacgggt ttttttaaata acttcccctt | 720 | aactccc 727

<210> SEQ ID NO 15
<211> LENGTH: 462
<212> TYPE: DNA
<213> ORGANISM: Sorghum halepense

<400> SEQUENCE: 15

| | | | | | |
|---|---|---|---|---|---|
| attggttttc | cttggatagt | tcagcactaa | caatgatgtt | ctgttctgtt | gttgatgttt | 60 |
| tcatgaacct | tgttgtgtca | taatctttca | ggatcttgaa | tgatgaaggc | aatggagatt | 120 |
| gttgatgaga | atgatcacac | atcgaatcta | cacgagaact | tgaactcttt | ataacaccta | 180 |
| tacgatcatt | ttccctctga | gctagcttct | gggattgagt | taggctcatc | aacggctcta | 240 |
| tttcgtccac | attgaaatcc | caatcatcaa | gactaataaa | atgatcaatg | tctaataagt | 300 |
| tcatttcatt | taacattttt | tgctcaaatc | ttttgaagtt | ttgaaagaca | agtttggtac | 360 |
| taatccatgt | ttatttgtca | ttcttttta | tatatgagat | ttgttttttgt | tttggagatt | 420 |
| ttgatggtat | tgtctgttat | ataagataac | aatatcactg | tt | | 462 |

<210> SEQ ID NO 16
<211> LENGTH: 510
<212> TYPE: DNA
<213> ORGANISM: Sorghum halepense

<400> SEQUENCE: 16

| | | | | | |
|---|---|---|---|---|---|
| tagatgaggc | aattcaagca | aaggacaaga | tgactcacgg | acctggcaat | gaatcagtga | 60 |
| aaaccaaaga | tatctgcact | atgaaggaga | ttccagactt | ccttttgtcc | gggaaaaggc | 120 |
| gcactggtgc | acataagttc | aatagggctg | tgtccatgat | cttcgcgga | ggtggtctct | 180 |
| atggggacaa | gaaagaggga | gttgggttca | ttgtgtatgg | gtctttcgaa | gacaatctcc | 240 |
| agtactgaag | attatactg | tcccgtactc | ttctaagtga | aataagtata | gcagcaggca | 300 |
| ctgttaatgt | tgttaatgaa | tgactcacgc | tggtaggatt | aatactgtcg | ttgtttgtct | 360 |
| ggatgccctt | aagcggaacc | tttgtctctg | ccctgttgaa | ggttattggt | ccgtatgcaa | 420 |
| ggtcacgctg | gtaggattaa | taaccctgtc | gttgtcatga | tctgttgacg | atttgtgtgg | 480 |
| atgctcataa | atatatgtat | tgttaagacc | | | | 510 |

<210> SEQ ID NO 17
<211> LENGTH: 404
<212> TYPE: DNA
<213> ORGANISM: Sorghum halepense

<400> SEQUENCE: 17

| | | | | | |
|---|---|---|---|---|---|
| acgccatcta | acaagatgtt | ggcttcaccg | ttttgtgaca | tgcatagggt | tatatttcgc | 60 |
| acatgcaaga | catccagcgt | ttccttatca | tgccagtcct | ataaagctaa | gggttacagg | 120 |
| acaccctaac | aaaaggtcgt | cctgcgaaat | aacacccatt | ccttagcctg | ttgtttgtat | 180 |
| attagccagg | ctatcgtaac | ctcagttaca | gttaggtaac | tattggtgtg | taatttagcc | 240 |
| aaaaaactgc | ctgtagatgt | atttttccata | ttgatatact | atatgtatga | ggttgaatgt | 300 |
| gctctgattg | tctttttatg | tcttattagt | cagcacactt | tctttatatt | taagatttta | 360 |
| tgtatcactt | cacacacgcg | cgatggcgcg | cgctcttcac | tagt | | 404 |

<210> SEQ ID NO 18
<211> LENGTH: 177
<212> TYPE: DNA

<213> ORGANISM: Sorghum halepense

<400> SEQUENCE: 18

| | | |
|---|---|---|
| gcacgagcca cctatctgtc ttccactttt ttctcagttt tattcccgta gcctttctcc | 60 |
| tctccctgta gcagttcatg tgagaagccc acaacagaaa attgatgact gtaatctgag | 120 |
| atttttgagt tgggaagtga ggccctaacc tcaccgtgcc ctctgggttt ttggatt | 177 |

<210> SEQ ID NO 19
<211> LENGTH: 322
<212> TYPE: DNA
<213> ORGANISM: Sorghum halepense

<400> SEQUENCE: 19

| | |
|---|---|
| gcacgagggc gagctcatct cccgcgacaa gttcaacgag gacgccgcga actatttcag | 60 |
| gaccgggcgt cagaagggat ccaaggccgc cgtcgacgaa ttccagtagc cggcgacgta | 120 |
| aggttaaaag cagtatatat acagcgctcc tctcgcctac atatatatgt gtgtagttcc | 180 |
| cacttcaagc ttgcagtata tacatgtggc ctgtgggcat gcatgtagga atactatatc | 240 |
| tactactact atattttctg taatcagaat gtacctagtg catgcatacc actatgtacc | 300 |
| tgtgcgtacg cagccatgaa gg | 322 |

<210> SEQ ID NO 20
<211> LENGTH: 851
<212> TYPE: DNA
<213> ORGANISM: Sorghum propinquum

<400> SEQUENCE: 20

| | |
|---|---|
| ggaaaggtgt tttttatatt tatataaatg ataggacttt taaaagtatt cacttttta | 60 |
| tgtgacaact tccgcttgaa tgatcggctg tcaaacatca aatttggca tgatcttgcc | 120 |
| atagagttta gtctctgttt tttagaatga tcattctgga cttacttata tgatatatgg | 180 |
| tattacatgg ttccttaatt gacgagatga tctactccct ccgtccctga aagctgcaat | 240 |
| ttctagagtt gtcttaagtc aattttttaa aattttgacc aaatttatag aaaaaaacac | 300 |
| taagatttat agtaccaaat taataccatt agatttatca ttgaatatat tttcataaga | 360 |
| tactcatttt ttgttataca tattgatgct cttttctata aaattggtca agttaaaca | 420 |
| agtttgacta gcacggactg tagaaattga agctttcagg gacggaggga gtatttaggt | 480 |
| accatgagta tctagatgca ccactgattt ggtgatttgc ataaaacagc catacagagt | 540 |
| catacagaat catagacatt gccacacatt taaagatagc caaagatcgt ggtcttgatg | 600 |
| attagctaaa aaataactta ttttcaccc tgatatctga aaactttgcc ctaacccttta | 660 |
| tttagtagcc aacgaatacc aatttaagt ttttgtggtc actggttgtg aatgtattat | 720 |
| aatcacatca cacaagtgat aacagtgctt caactatttg catatttcaa ttccgtagaa | 780 |
| taaaaatcat ttacctatca gaaggatatt aactaacacc aggaatgatc aaccatgctc | 840 |
| ctagagttag c | 851 |

<210> SEQ ID NO 21
<211> LENGTH: 742
<212> TYPE: DNA
<213> ORGANISM: Sorghum propinquum

<400> SEQUENCE: 21

| | |
|---|---|
| tagcacgaac tcgctcggtg agccaagcag tgtgctcgct cggaggagca tatatagctt | 60 |
| aatttgctgc tagctagctg ctaccacgca cactgcactg acgacgatcg atcgatcgag | 120 |

```
caagtagctc gatctgctag tagctagcta gctagtgatc gatcgctcct cgatcgttgg    180
tacggtgctc gatcgatcga ccgtccaaca acgtacaagg ccggccatct atcatatcat    240
atcatatcat ggctctagcg tcggttgcca aggttgttct tggttccctg gccttcggtg    300
ttttctgggt gcttgccgtg ttcccgtcgg ttcccttcat gcccatcggc cggactgcgg    360
gcgcgctgct gagcgcggtg ctgatgatcg tgttccacgt gatcagcccg acgacgcgt     420
acgcgtccgt ggacctcccg atcctgggcc tcctcttcgc caccatggtg gtgggcagct    480
acctcaagaa cgccggcatg ttcaagcacc tgggcacgct gctggcgtgg cggagccagg    540
gcggccgcga cctgctctgc cgcgtctgcg tcgtcacggc gctcgccagc gcgctcttca    600
ccaacgacac ctgctgcgtc gtgctcaccg agttcgtgct cgagctcgcc gccgagcgca    660
acctccccgc gaagcccttc ctgctggcgc tcgcgtccag cgccaacatc ggctccagcg    720
ccacgcccat cggcaacccg ca                                             742
```

```
<210> SEQ ID NO 22
<211> LENGTH: 762
<212> TYPE: DNA
<213> ORGANISM: Sorghum propinquum

<400> SEQUENCE: 22 ggactctttta ctcactgctg ttactttctt gtatgaaatt tcttttttaaa aaatagacta    60
cctaggagga actagtttct tgattttgca ttaagaagag aatagaaacc tggttcaaat    120
tgaactggac tcaaacctag atggtgtttt atgcccacac ctccatccaa ctgagatagg    180
ctcactttct caaaattcat gattgatctg aactactgta cattttgtta atgtatacac    240
ctccacacct tccaccaact gaggtaggct cagtcggtgc atatttcata ttggtctgaa    300
gtacgccaca ctatgtgttt tgttaatgta ctgccagtat cacatctttt gtacacgtgt    360
ttgagtaaat aatgtctatt cttttttggaa gatatatgga ggtttaaaaa ttacgaacac    420
acaggtttgc caggaacccc tgaaagatgt attatttatt aatatataaa acaaagcctt    480
atttttgttc ccaactgtaa ccctgtgcaa taggccttaa tgtttagcct gttcatattt    540
gtttgtttag accctatatg ctgacttact gttctgtcct ctttataagt agtagtaatc    600
ttatcaaaat attttgttt gtgcagggaa ctagcaaaag attttgtggt ctctggtact    660
gcttcagaat cactttacgg tgcttgtgag tccatgtata agccaaacat ggttagtttc    720
tttacatgag aactctgcag cagatctttta agactttaac tg                      762
```

```
<210> SEQ ID NO 23
<211> LENGTH: 584
<212> TYPE: DNA
<213> ORGANISM: Sorghum propinquum

<400> SEQUENCE: 23
gatgcctgtt aatgggtatc ttcccccctac cattgggttt agatacaggc ttacatgtct    60
tgtcttttat catcagattg ctaactaatg aatggtactg catattttc ttccgatctg    120
caagtcctgt attgggaaat tgtattgttt tcggaagcac cgcagaaact taaaggtgta    180
taattgaact tgaaatacca tgtggtgcct gggctacatg tacaggcaga taatgtgtca    240
agtgcgcttt ttttgagcta tttttgaaat tgacataatc tcattgtcat agttttcttg    300
aattatgtga gacttaatta aactaaagct caatgagtcg aactgaaatc aaaactaatt    360
catctatgtt ctaaaaggaa aaccaaaagt tattcaaaat ttaaataaac aagacatata    420
```

```
tgtcattggg atgttacttc tcaagacaaa ctcaatgagg tcgctaatct gtatgggaac    480
cgtgctataa cagggtttg atttgattta ccaatgaaaa gtcgtaagcc taatggagtc    540
cacctggaca aagcaggtcc taaccacccc tccaagacaa gtac                    584
```

```
<210> SEQ ID NO 24
<211> LENGTH: 836
<212> TYPE: DNA
<213> ORGANISM: Sorghum propinquum

<400> SEQUENCE: 24
tgcatggcct gacgcgcgct ttctctttca gcgccgctct gatccctttg ctcgctcgta     60
gtattgtctg aaccgaggcc atgcatatgt accctgtgtt ttctagtgct tgccgatggg    120
aggcagccca gccagctgca tgcctgcctg cctgcaactc atcgatcact acttgagtac    180
ttggcgtcaa gcttactact ccctccgtct caaattaaca ttccaagaat cttggagagt    240
taaagttttt caagtttgac taaatttata tagcaaaata ataacatttt tggtaccaac    300
caagtatggt tagattcttt gttagttata ttttcatagt gtatctattt tatgacataa    360
atctttatat tgctctctat attttttgtt aaacttgaaa atgctttgac tctccaagat    420
tcttggaatg acttataatt tggaacggag ggagtagtaa ataatatatg taagttaatt    480
acctctgtca atgactaata tatatagcct gtctcttgct tccgagtgta ctctattagc    540
tagctagcta catattgcac gttgcttcct ttgtactact aatgtatagt actaggagct    600
gagtgagagt tagtgagttt atatatattt gggatcacag gttaatctgc aggctgctta    660
ttactagttt actactagta tggtgtacag tactactata gccgcataga taatactact    720
gcttctcttc tctgtgtact tacacttgca tgcatatgac tatgtgagtg accgagcact    780
ctactcttct tggacgttac tcgtcgagtt ggagctagcc atgtctccga tcccgg        836
```

```
<210> SEQ ID NO 25
<211> LENGTH: 966
<212> TYPE: DNA
<213> ORGANISM: Sorghum propinquum

<400> SEQUENCE: 25
aaccaaccaa attcacatgt tccgattgtt taatgcgaca tgacaagctc aaacgacttg     60
ttcctgttac catttgaaaa ggctcgccgg gatctcaaat ttattgtgga caataaataa    120
ataaataaac attctaattt catttccaga tctactactg taaatatgat cagacaagcg    180
ggcagacgcc ggttgagctt gagcctctgc ctatactcct gctgaataaa caacaactgc    240
agggcaacaa ttacacatac agctacgaaa cagccacttt acatccaaat ccaccactgc    300
aggatggatt gctagccaca atttgccaca ctttacctta ggcaagtttg accaagttag    360
caagtgtttg attcacaact aagcttaggt atgatttttt tgggctccac atgtcataga    420
gttaaaaagt gtggcaagat tcctttaggc aagacaaagt gtggcaacgc cacacatttt    480
gtggcttgcc acacttgcct aaaattagtt gtggtagatt gtgactggca accaaaacat    540
ccccgtacta actaacgtct caactcgagt ctcgcagtac ctataaaaat gcccaatgtc    600
agtcactcga aaatctgggc agaatggttc agcatcgccc actttatatt atactactct    660
agcacgagca tccctactgg tggtttcagt cttcacgtta tcatcggcat ccgcatcagg    720
ctcgcactgc ccgctttcag ggccagagac ctcccctggg ctccgtttct gactatcctc    780 cacccccgccg ttgtcggaat ccattggtgc cgctccttct tctgggtcgc cacccactgcc    840 acctccgtca gtttctggtg tcgcagcaac ctgcacagag cagtccatag caacaatgta    900
```

```
gacatgacat tgtttgtgtt tacagatgat gttaaaatga ctagttatga tcaagaagac    960
agtcga                                                               966

<210> SEQ ID NO 26
<211> LENGTH: 917
<212> TYPE: DNA
<213> ORGANISM: Sorghum propinquum

<400> SEQUENCE: 26
aagcgccact tcacttcgga cctgactact ttgatagttt gatgagtgct caagtaggtc     60
aatctgtttt ttgaggcaaa gtaggacaat ctgttttttg aggcaaagta ggacaatctg    120
ttgtaatagg agctgctctt cttttttcgg gttaggtgct aggtgctagg tgttgggtcg    180
gtggtaatcc tgggattact gttggccggt tgtgtacttt aaactctact tcctctcaat    240
ctgttgacac ggtcgcgaaa aagtaggac aatctggact tccctgtgct ttgtagtcct     300
gcagattctt aggacctgtt tggcaggctc atctagagga gccctgccaa acgttttttc    360
tgtaagccgt ttttgagtaa aaaacagatg agccccttag tattctgaat atctcagttt    420
atttaacctt tgcagcagaa gatagcagta tgtttggtcc taacttagat atatgtatct    480
gaaagcttaa gtattttttg aagagaagat gtctgaaaac ttcagtgacg acatgggttt    540
cagctatagc agtcttacac gtccttttt tcgcgatcgg gtgattagcc cgttttccat     600
taagaggaaa gtaaccacat gttacaaagg ggagacagtc ttacacgtcc ttaaagacag    660
agaagagatt aattcaaagt ttagaaagaa taggtgctat gggcgcatct tatcatttat    720
atggggaggg gaacatatat tgtgaaaatt ggaatattcc cttactaagt ctgtatgatt    780
gtgacatata tgtagtagta tataaataca tagaagggca gcatgcattt acatgtattt    840
agcatgccag cgcacttctg aagaatgaag tgtgatgaat gctgaacaga ttgagttctg    900
tttcagttgt gatgagt                                                   917

<210> SEQ ID NO 27
<211> LENGTH: 651
<212> TYPE: DNA
<213> ORGANISM: Sorghum propinquum

<400> SEQUENCE: 27
agcgcagccg caaagaatgt aaactttctt cttcctcccc agacgcacag cagtaacaac     60
aactatactt gtggtcgtgg ctagcttgct gtctgcgtgt cttgtgattt gacccatcac    120
tttacaatgt cagcatggac acagcgacag catgtgtctg gtgctggctg cttgtgcctg    180
ggtgtgggct ggctctgttt gctgccccac cggcacagcc aaagcataca gatagtgttc    240
gttttttttt tgatgaacga tagtgttcat tttcagtatt tgcttcgaag tactctatac    300
taatgcgaac ctgattttgc attgtcttcc tctcatttgt gtttgttatc agtgggccca    360
tttcccacac atccacttcg gcctcatgcc ggaccagggc tcaagaaga ccttcaagac     420 tcaggtatca aatataaagc tgacattgaa aaccctagta actcgatgta tatttgtatg    480
tctccaaatc ctcacttgac actttgcacag aattcagagc atccagcagc aacactatat   540
tattacaata tatattatat atgcttctct tgagtttagt ttagtaattc aaagttttgt    600
actttgtaag cacacaccca tcttaatttt agctgtttcc tgggctgtga t             651

<210> SEQ ID NO 28
<211> LENGTH: 678
<212> TYPE: DNA
```

<213> ORGANISM: Sorghum propinquum

<400> SEQUENCE: 28

| | | | | | |
|---|---|---|---|---|---|
| cgttacgaga | cgcaatgtcc | gcgtgaccgc | agaggtgccg | acgcgtcgtc | gaccgaggtg | 60 |
| gcggggtgcc | gtgtagcaga | gcaggactgc | ccgccgggcg | tcttgggcag | aagatagaga | 120 |
| tctgagaagc | cgtcggcccg | tcgccctccc | tctcaactcc | gctcctctct | ctgttcccaa | 180 |
| cttcccatcg | ccgcattctt | cgcctccac | cacagcagct | tgagctcctc | accgccgccc | 240 |
| ctccctccac | ttccaccgct | gtccttgccc | tcctcgttac | cgtcagggtg | gacgcatcct | 300 |
| ggatctggcg | agcgcgtctt | ccttgcgcac | ttgatgaccg | cgtcggcgc | cctccaagca | 360 |
| gctccgattt | gacgagaccg | tcgacgccgg | tcgaaccaag | acggagacag | gccatcaata | 420 |
| cccagtagaa | tagcaaggct | gggcggctgg | cggcgtccag | ctgaggggga | gatagaccgg | 480 |
| cgcggcagcc | gagtcggacg | gagctcggct | gtccggagaa | gcgcacgcac | gacggggcac | 540 |
| gccagggatc | tgcagccgcg | gtctctcata | ccagtgatca | ggcttaatct | gggtggggaa | 600 |
| agtttggaaa | gatcaattcg | gtgaagaagc | acgattcaac | agggaggagc | ttcaatctgg | 660 |
| tgggcagaat | ttcgaaat | | | | | 678 |

<210> SEQ ID NO 29
<211> LENGTH: 704
<212> TYPE: DNA
<213> ORGANISM: Sorghum propinquum

<400> SEQUENCE: 29

| | | | | | |
|---|---|---|---|---|---|
| tcatactacg | agaggacctg | ccctatgtac | caggtaggta | gtagttaacc | tactactaat | 60 |
| taacccagga | aattctgcgg | taattcttgg | taattcttaa | gccgcgaacg | atgcggtaat | 120 |
| ccataactac | tagttaacct | actttaccct | gtgttcatg | caacggcgaa | cgatggagca | 180 |
| gagccagtgc | atgaccagcg | agaagagcca | ctactccggg | acgatgaacg | ggaccatctt | 240 |
| cgtggtggcc | ggcggcggcg | gctgccacct | gtcgagctac | acgacggcga | tcccaagtg | 300 |
| gagcatctac | cgcgaccatg | acttcggctt | cacgaagctg | acggcgttca | accactcgtc | 360 |
| gctgctgttc | gagtacatga | agagcagcga | cggcaaggtc | tacgactcct | tcaccatcca | 420 |
| cagggactac | cgcgacgtgc | tccgatgcgt | gcacgacagc | tgcttcccga | caacgctcgc | 480 |
| cacctaaggc | ctcgttcgtt | tggcatggaa | tcaatgcttg | gaatgaatcc | tgctagaatt | 540 |
| gctttggaaa | tttatataag | cattgatcaa | atggagtaat | tcctggtgaa | atcctgcaga | 600 |
| accgaacggg | gcctaataaa | gccattgtta | tgacactact | agtttggct | tggtcgtcca | 660 |
| ataaaatgtg | tcaaccactt | agtataataa | tgtgctctgt | gaag | | 704 |

<210> SEQ ID NO 30
<211> LENGTH: 427
<212> TYPE: DNA
<213> ORGANISM: Sorghum propinquum

<400> SEQUENCE: 30

| | | | | | |
|---|---|---|---|---|---|
| tgttcttgac | ctcttttgga | ttggatggta | gtgccctgat | cttaagttat | catgttctta | 60 |
| atcaattctt | ggaacttcaa | taggttcact | gatgagctat | cgatgtagtg | cgtcacctgc | 120 |
| tgttggtgcg | tcaggtgcca | tttttggatt | ggtatgtcta | cttctcctcg | cacttgtgct | 180 |
| cattacccag | tgccagaatc | atggtacccc | tatagtgtgg | tataattcac | tagcaacgtg | 240 |
| gaatacaaac | tactccatct | gtttcaaata | atagttcact | ttagatttgt | cataagtcaa | 300 |
| atgcagctaa | ctttgaccaa | gtttatagaa | aaatacatca | acatctacaa | tatcaaatta | 360 |

```
gtttcattaa tttctccatg aaacatggct tcattgcaca cttatttgaa cttatagatg    420
ttaacat                                                              427

<210> SEQ ID NO 31
<211> LENGTH: 674
<212> TYPE: DNA
<213> ORGANISM: Sorghum propinquum

<400> SEQUENCE: 31
ctaccatttc gatttggctg cttgtttgat ttctatttgt tccgttccct tctgaaatgg     60
tttgattgaa atgcgtcagg gattaattct tgctttggtg acatctcatc ggattaatct    120
gtaatagttt gtgtccttga cgcctcgtat gacattatag cctgtcattt agttgacaga    180
gttctctatt tgcatattgg actatcagct tggttaacca attggatgca tctgtctgat    240
actctgaaag ctccacaaat aatattaagg gtgcacattg gtatctttta ttttccccc    300 ttattattga ttgctttgtt ttacacaaat attgtaacac caggtgagca tgttatggga    360
ttgttatctg tatctggtaa taattgttct agtcaggaac tatctagaga atagatacac    420
tgatggaatt acttcattag tttctcectg tgacactgca agaggttgtc ttgtcatgta    480
tgactatact aaaatggctt tcatctcaaa gggaaaacga tggcttaacc ttggatattg    540
agcaagtttt tacagtatta atatgggatg ttagccaact tctcctgagc tacactgctt    600
agactgttga agtccggggg tcaaacaaac ccctgtcacc agttccagtt ttgaaggcgg    660
aacaaagttc ttaa                                                     674

<210> SEQ ID NO 32
<211> LENGTH: 707
<212> TYPE: DNA
<213> ORGANISM: Sorghum propinquum

<400> SEQUENCE: 32
cctcagaggc tcttcatgag caaaaccaac cgcccaccaa tttccctgcg ccgccttgtc     60
aagttcatgg aaggaaaggt atgcagttga cagccactcg agaacagtct gttattccga    120
aaatgtaatg caatatgctt gtctcttttt gcacctgcta tgtaattgtc atgttagttt    180
tatgtatgtg gcatgaaaaa atagctgaaa agcaaaatgg ttaatctaga tggtttgcac    240
ttagtttggt acatttggta taatggccat gaaaatggcg ctgaaatagt gtctaatatg    300
ttaacaggag gagaagaaca ttgctgtgat tgttggcaca gtcacagatg acaaaaggat    360
ccaggaggtt ccagcaatga aggttactgc cctgaggttc acagagacag caagggccag    420
gattgtcaat gctggtgggg agtgcctcac atttgaccag cttgctctcc gtgctccact    480
tggcgagaac acggtatgtt ttgtttaaaa tgttagatag tttgccaatt taaacaaaca    540
gcacatgttt tgaatgctac aagttgagtg aacattagtc tgcatgtctt aagccatagt    600
aattctcaac agatgtcagc tttatgggcc taacattctt aaaaagtgtt attgtaagtt    660
tgtcatgcta gtactgacat tgctcttgtc gtttggcagt actcttt                 707

<210> SEQ ID NO 33
<211> LENGTH: 816
<212> TYPE: DNA
<213> ORGANISM: Sorghum propinquum

<400> SEQUENCE: 33
catatggatt tcaagataca ttctcgaggt acctcaaaca ataattaagg atttcccca      60
```

```
tatcgtgtca ttttatttct ttttcttctt cataattatt agagcataca gtattttaca    120
agttcggcac cttattgtag taaggcattt atgattacac acagcaacat atcacgattg    180
aattaggcat ttgagaataa ttttctccgg gtgaaaaatt atatttcatt ttatctgtat    240
tgttcaaaat atgaggcctg aagcccatga tttcaacctt tagttaatac caattttac    300 atcaccataa acacttctaa atattgtcct actcacctt atcagagaat cacagagcaa    360
gctggggttg tccttaccct tgatccaaaa ccaattcagg tatgtccacc agtaagttgt    420
ttcgaatcat tacaatgtaa taggattaaa gtaatcttaa catattggtg acagggtgac    480
tggaatggag ctggctgcca cacaaattac aggttacagt cttttatgat aatgcttcat    540
ttccttccgt tgtttgttca tggtaatttt gtcattaacg acagacacc agaatgccta    600 tagcagtata atttaccata tgctgacttc tgagtgttaa aggaaaaaag tttgttctaa    660
tgttctagaa agggagtaga agtgaagtat tagtatatca ttaataaatt gttgtctagt    720
gtgattggat ccagatgatt gtccattcgc ttctattaat tactaacttt cgttatttaa    780 tattttctc aacacatttg acacactggg actgac                               816

<210> SEQ ID NO 34
<211> LENGTH: 686
<212> TYPE: DNA
<213> ORGANISM: Sorghum propinquum

<400> SEQUENCE: 34
ttcggcgact ccaaaacggt gagctatagc catcgagttg cttacatgca gctgcatatg     60
catcgccaac aactaaaaca ataaaatttt ttccagtggt gtgtttcttt gttggtcgct    120
ttcagtttca gtggtctccc tggttctgca gttgttcttt tttctgatgg ttgtctggtt    180
aggtaggtgt agtggcaggt tttcgaaagc aaagctgctg gggcctgggg gactagtgct    240
gtaattttcg aaccttttt tgttttttccc tcgtctaata tatactaata tacaccggca    300
aatctcttga tgttctttct aaaaaatata tacacgacgt cttctatcca aattaattaa    360
aacagcaatt tttttaaaaa actcttgtta ttgtatatgt gtgtatatag gtgtcgctgt    420
gcgtgaagag gctagtctac accaacgatc aaggggagt cgtcaaagga gtctgctcaa    480
acttcctgtg tcagttttct ttcctctctg tgtcttgttt tagttcgaat ttgatttaat    540
tgttcgatgc agactaagca taaaacctgt caaattaagg gttagagtca ttttcaaggc    600
atcggagacg tgtgttcaga ggatctcgct agtacgctga ctgatatata tcctgtgcat    660
gcaggtgacc tgaagcccgg ctctga                                         686

<210> SEQ ID NO 35
<211> LENGTH: 688
<212> TYPE: DNA
<213> ORGANISM: Sorghum propinquum

<400> SEQUENCE: 35
ccatcctcag tcactcaaca gtgtctgtat gaaacaaatc tcctgatact actggagctg     60
ttttcctaat tgtgcaccaa aatcatgtgc tacaacacaa ccttaataaa ttactgtgtt    120
tgccttgctt gcagacccca agaagcagct tgagttggca gtgcgggctg tgttcaactc    180
gtgggagagc cccagggcaa agaagtacag gagcatcaac cagatcaccg gcctggtcgg    240
cactgccgtg aacgtgcagt ccatggtgtt tggcaacatg gcaacacttc tggtactgg    300 agtgctcttc actaggaacc ctaacactgg agagaagaag ctgtatggcg agttcctgat    360
caatgctcag gtatacttat ggtgacctca gtcaggcttt catccattgc tagctcctgt    420
```

```
ttgatcctga accttaatta gcttctgtgt tctgttcata catgaataca tacatgatta      480
cctgacacat gtcctggttg gtaaacgaaa catgctgtgg atcggacatc ggagtcaaaa      540
aatgaatttg ccatcataca attttgtttc ctatatattc agggtgagga tgtggttgct     600
ggaattagaa ccccagagga tcttgatgcc atgaaggacg tcatgccaca ggcttatgaa     660
gagctagttg agaactgcaa catactgg                                         688

<210> SEQ ID NO 36
<211> LENGTH: 667
<212> TYPE: DNA
<213> ORGANISM: Sorghum propinquum

<400> SEQUENCE: 36
gtaataacaa gtgaaatgaa caactccgga gacgacgata catgtggaac ccataagcag       60
atttgtcatg gaccactggc ccgttttttcc tgagttttgg acgataattt gattggtgag      120
agaggcaaat catcgcactg gccttgtcat cacacatata cgtatgtatg agggagagaa      180
cgacacttgt actgtcttgc aggaacttgt ttcgtttttt ttttattttt gttttatttt      240
tagttaataa aatggctgaa cgtactgccg cgcgcttcaa ttaattccct gatcaactct      300
attttgcgca tggatatggt gtgctcgatc atggacgtac gcacgcacgc agtggccagg      360
agcatactgc gagcagacca acgctggatg ctgcaagccg acgaccggcg tctcgccggc      420
gcgcgacttc tacataacag gcctcaccgt ctacaacgcg accaccaacg ctgcactgac      480
ggaatgcagc aatcaagctc cttacaaccc taacctggta cgtccgtaga ctctcgcttg      540
tgcacatcta gtgtttgtcg tcgtaggtgt gacaccgtac ctttaatgtg tacgtgtgtg      600
tctgtgtgca atgtccatct cgacagatta ccggcatcgg cctggagcag tactggatca      660
acatcaa                                                                667

<210> SEQ ID NO 37
<211> LENGTH: 724
<212> TYPE: DNA
<213> ORGANISM: Sorghum propinquum

<400> SEQUENCE: 37
cgcttttttc atgccatgcg acgatgattt gttaggtctg gtagcgtgtt ctcgcctgtg       60
tttcgtggta aagtttgggc ggctcaagtt gatcctggtt tagcggtgat caccatgctt      120
agtacaccac caatcgaagt gtttgtatga ttcgactggt gtttaatggg cttagtata      180 tacatgatga ttcgtcgttg tttaggttgc tgtagtctcc tcgcatctta ttttgcactt      240
aggttggctt aaatctattt tttgctcaat tagatctggc agagacaaag tgcgtagggc      300
tatccgtctt agaaatactg agtcaaatgt tcagctctag ctgaaaattg cctatagatt      360
tctcttgcaa ctggaagttt tccgccttcc tcttgcaatc ctaagtctta cgcatatggt      420
cagatgatta ttttttctcct tgtctaatgt tgctagggaa tctcacattt ggcagttcat      480
attgattgtt taggcgaagg gaaatggcga ccgttcctgg ggatctgatc tggcaggttg      540
tgaggaagaa caactccttc cttgtgaagc agtttggcaa cggcaatgcc aaggtgcagt      600
tcaccaagga gcccaacaac ctctacaacg tccactccta caagcactct ggtatgctgc      660
ttcctgtgaa gtttctggat gtcctgtata caaaacacct tgtgatttta gtaataaata      720
ataa                                                                   724

<210> SEQ ID NO 38
```

<211> LENGTH: 2837
<212> TYPE: DNA
<213> ORGANISM: Sorghum propinquum

<400> SEQUENCE: 38

| | | | | | |
|---|---|---|---|---|---|
| tactctcaag | ttctttgtac | cgtaaagcaa | aaatatttta | atgatctatt | tcggttttcc | 60 |
| tagctcttta | taagctgcaa | tagttgggaa | gctagctagc | tcatgaactc | tttaaactct | 120 |
| atctagttaa | gtagttttag | agcctatgag | atttgttgtt | cgctaaaaga | tggatccgcc | 180 |
| catttgccgt | gctgaaatgt | gtaaggaagt | tcttcaaata | taatcggtac | ctaaggaacc | 240 |
| acccatttgc | ccttctaaca | tctgtaagga | aagttttcca | aatataattg | atagcatagt | 300 |
| actatagaaa | gcaacccttg | accggcctag | aaacaacttt | acgtcgaaga | taatctcacg | 360 |
| ttgtttgtac | tattgtgtaa | ataatagagc | agaattttct | tactggtcta | ttttgatata | 420 |
| agctgtaata | gtttcttttt | tttgcacgaa | agaagaatta | tattaggata | atagctgagt | 480 |
| atatgaatac | gttacaagca | ctctaaatta | caaaaatatc | caaaaaatca | tctaaattat | 540 |
| atccaagctg | tgaatagctc | caaatctcaa | atcaaacttt | gtgtgacgct | ttgcataatg | 600 |
| gatgaacaca | gaatcaaaca | ctcgacaaaa | ggcctaagaa | tagatgtcca | acgaacaacg | 660 |
| gccaatattt | atgtagacgg | aggtgagaaa | cttcatcttt | ctagcgttat | ttttcttctt | 720 |
| ctttctgcca | ccgaagaaag | agaaagacta | atctgaaact | tattatccct | agcccttcat | 780 |
| cgtggccaga | tctaaccacg | ataaaacgta | gaaaagacag | aagaaaatta | ttccatggcg | 840 |
| gtgacaccat | ctccgtcttg | atgtcgccat | ctgaaaataa | aagtctctat | gtcattaaat | 900 |
| cggtgaggat | gccgacgccg | tagttgttgt | ccgcatcttc | aacggagccc | ctacggagaa | 960 |
| aacggttcca | ccctaccatc | tcactgtcac | cggagaagag | gagaatgaaa | taaatcgtca | 1020 |
| aaactaacaa | atttgacata | gagagactct | aaccaaaaga | cttgatctaa | ttgaaaaaaa | 1080 |
| attattaaaa | ataatggatc | gtcactctct | tcgacctccg | atcactggag | aaggaagaaa | 1140 |
| gggggaccaa | caatgataga | cgggagtcat | tgtaagttga | aatagctagg | gagctaacaa | 1200 |
| ctctagtggt | tggatagtta | atattccata | tattctaaat | tacaagtcat | tctaagaatc | 1260 |
| ttgaagagtt | aaagtatttt | caagtttgat | caaaatttata | gaaaaaatac | taaaatttgt | 1320 |
| aacgtaaaat | gagtatacta | taaaaatatg | attaaaaatc | taatgatgtt | tagttggtat | 1380 |
| tataataagt | attattttat | cgtataaatt | cgatcaaact | tagaataatt | tgactcttta | 1440 |
| atatttatgg | aatgatttac | aatttagaat | gaatggggta | tatatatgta | ccgtctgttt | 1500 |
| cggttacaac | tttttatttt | tttggttgct | aacttataaa | aagccagaag | gatccgaagt | 1560 |
| cctgagaaat | gtgacaagag | agaaaagctg | atcgggttgc | ctttaactat | atgttggaat | 1620 |
| gcatctgatt | ttctgcagta | tttgttaaaa | gagcctatga | aattcataag | ttactcccag | 1680 |
| catctaattt | tctgcaacat | ctgttaaaag | agctgtgaat | gtaggagtat | tattatggca | 1740 |
| gtgcagaaat | aatacactcc | caggccagca | ccatcaaaat | aagaagggca | ttaaaaaaag | 1800 |
| gtgcttttgt | tgcagtgggt | gaatccaatg | tggaaactga | ttttagggac | cgaacaaagg | 1860 |
| ccctacgcca | ccaccagtac | tccacacaca | aattaggatt | ggtagagccc | atccctgcgc | 1920 |
| cctgccttgc | tggctctgac | ctctccctcc | cctcccctcc | cctccctctc | ttgttgctcc | 1980 |
| cccttctttt | tattgggttt | tttgtcttct | tggatttgcg | cttgtgctca | cctgggtggt | 2040 |
| gcatactagt | ctctgcatca | gagaggagag | acctccgagc | tgggggctct | tcaacatata | 2100 |
| gattgggctc | ttcaacatac | agtttgcctg | cggggagaga | gtgaaagaga | gagagctcaa | 2160 |
| ggtgggggca | aaaggagaat | ttttatccca | gcttcttagc | ttgattctcc | ttgatcccgg | 2220 |

```
agagcagccg ccagtccaac taatccttgc tgttggcgtg ccggggcttt gattgctctc    2280
cagatctgag gcacctgctc ggtggattcc aggaatccga gcacgaactc gacaggggag    2340
ttctcaggga aaaggtgagc cccttttttcg tctccttgct catccgccca ccattgccaa    2400
accgtctgtc ccctgtccac cactgcagta atcgcgtagt cttagctccg attgttaagc    2460
ttcagctgct gcctcttgat ctgtttctgc tgcctacact gggcgacgct tgatgcatac    2520
gagataatga gttggccgca agtttctttt gatcccagca tacgatccac cagctcacgc    2580
gcgcacagaa ttttttgact tttttttaac tcgctttgat ttgattgcat ctattgtttc    2640
ggttgcgcag gccgcagggg attaaggaag aggctgaaag gcggtggag ataataagac     2700 tataagagcg agctgggccc cttcccttga ggatgccgtc aagaaaccgc gtggagggga    2760
gcgcgatgag atgagggatg ctggccgcgg tgatggacta cttcagctcc tgctggggcc    2820
cgcgatcgcg tgccggg                                                   2837

<210> SEQ ID NO 39
<211> LENGTH: 518
<212> TYPE: DNA
<213> ORGANISM: Sorghum propinquum

<400> SEQUENCE: 39
gcacgaggct aacacaaaca aggtcccagc cagagccagc agcagcgact acacactcca     60
ctctccctcc ctcgctcccc tcggacaggc cgacatgggg cgtggccgca gcagctcttg    120 gccaccgcg gctcctgcgc tgctcctcct cctcgtcgtc tgcttctccc acggcgtggc    180
agcggctcgc ctcctgcctc cgctgcagcc agctacagcc gttcctccgc aggttcttca    240
ccaagcggag aatgttgtca tggcggcagc tgccgacggc ctcgtgcttc aggaaggtga    300
ggccgtgggt aatggcgacg agctctccat ctcagagatg atgggagcag aggaggaggg    360
ggcggcggcg gtctgcgagg gcgagaacga cgagtgcctg gagaggcggc tgctcgggga    420
cgcgcacctc gactacatct acacgcagca caagggcaag ccgtgatcgt gtcaccgtga    480
ggaggaagac atgcatctcg ccttgccggt ttggtttg                            518

<210> SEQ ID NO 40
<211> LENGTH: 518
<212> TYPE: DNA
<213> ORGANISM: Sorghum propinquum

<400> SEQUENCE: 40
gcacgaggct aacacaaaca aggtcccagc cagagccagc agcagcgact acacactcca     60
ctctccctcc ctcgctcccc tcggacaggc cgacatgggg cgtggccgca gcagctcttg    120 gccaccgcg gctcctgcgc tgctcctcct cctcgtcgtc tgcttctccc acggcgtggc    180
agcggctcgc ctcctgcctc cgctgcagcc agctacagcc gttcctccgc aggttcttca    240
ccaagcggag aatgttgtca tggcggcagc tgccgacggc ctcgtgcttc aggaaggtga    300
ggccgtgggt aatggcgacg agctctccat ctcagagatg atgggagcag aggaggaggg    360
ggcggcggcg gtctgcgagg gcgagaacga cgagtgcctg gagaggcggc tgctcgggga    420
cgcgcacctc gactacatct acacgcagca caagggcaag ccgtgatcgt gtcaccgtga    480
ggaggaagac atgcatctcg ccttgccggt ttggtttg                            518

<210> SEQ ID NO 41
<211> LENGTH: 728
<212> TYPE: DNA
```

<213> ORGANISM: Sorghum halepense
<220> FEATURE:
<221> NAME/KEY: misc_feature
<222> LOCATION: (1)..(728)
<223> OTHER INFORMATION: n=a, c, t, or g

<400> SEQUENCE: 41

```
gagaaacctg ttttttaaat tacatccatg cagtatagaa tcgtagtagc aagtttagta      60
gattgcagcg aggttattca actgcactta catacggcag cggtcaaact cgtcaccggc     120
gccggataat gcgaatgaan tgtggccatg gcttgacatg ggctggcttc ggacaggcct     180
ggcgggcata aacataggta acattatagc agacacacat cttattcagt tgagacttat     240
tccaactcat atacaacatg aaacgcctga caagatgtcc tccctaggg atgataagat      300
cagatcagat cagatcagat caggctactg ggctttgtat cccaaacttg ttcatcaagg     360
cagcaagctc gagacggcga tcccccagg tcgctgtgta ggcatctatc ttgttgagct      420
cctctatcca ctccttgagt ttaggccttt cttgtgtcat atcgtagtgc ttcactgcag     480
cgaagaaatc cttgaagcgt tcgacaaagg gcgcataaac catgtcgact gcgctcatgg     540
actgccccag gagaatggcc atcagagaac tcccaggatc tccactgtca aacagacaat     600
acttatgttc atcatcttgc tcgcaggcct cctntaagat tttttatttt tatccggtca     660
tttaggcccc ggnccatttc tagtatatcg aaataatctt tttttacaaa aaaatattg      720
ccaatcct                                                              728
```

<210> SEQ ID NO 42
<211> LENGTH: 821
<212> TYPE: DNA
<213> ORGANISM: Sorghum halepense

<400> SEQUENCE: 42

```
tttttttttt tttttttttt tattacaagg atgactcaaa gatcacaatg cattgttgaa      60
atgtgttcag agtttagaca tagtagactt tagcatgata gcagcacaaa gatcacaatg     120
cgttcttctt tttttttctg aactgttggc agcatattat tcattctcaa caacacaaag     180
atggtttcct atccgtcttc ttctcttcca cggctgtat gttcttagac tgctgtctta      240
attggcaggg tgcagtggcg tgggatgtga attttccata gcggagctgc cgccgttgcc     300
actgtcgcca ccacgcctca gcttgagagc gagcaggacg cgttgtaga tgtcgtggta      360
catggctctg ttgatggcct ccacggacgc ctcccggaga gcgagagcct ccgtgacctt     420
cgccctgca gcctccgtct ccaacttgtc gtacatcgcc gacaggtcca gcttcacctt      480
gcaccagtac gccacccgct cctcaatcaa gtcaagctcc ttattcttat cgccggtgcg     540
gctcgccggc gcaccaccgt cgtctgtcct gacgacggtc accatggact cgccgagcag     600
caccttcttc ttgtccatgt ccgagctctg cttatacacc cctccaacct tcagcagctc     660
catgacactg tcgccatcat cggtgccggt gccgtcctgc tggccttctg cagctggaac     720
atccaggtag acggtgaact ccttcaattc tccggcggag acatcgccga cgacgacctt     780
gccggacgtt ttgccgccgc cgatttcgct cttgtagaaa a                         821
```

<210> SEQ ID NO 43
<211> LENGTH: 246
<212> TYPE: DNA
<213> ORGANISM: Sorghum halepense

<400> SEQUENCE: 43

```
gcacgagata ataaaggtag ttaactaggt aattaagcgt gtgtgtcact agtaagactg      60
```

```
tgtatgtgtg tgttactact ttaattacta gtataagttg gcattggctt cgttgccaag      120
tgtccggccg gcaggtatgt tttcgtgttg cgacacgtgt tcatgtctat tgtcatatgt      180
catgtgcatt gttgagttcg ctggattaaa actatgatt aaaattattg tttactgatt       240
tattgt                                                                 246

<210> SEQ ID NO 44
<211> LENGTH: 421
<212> TYPE: DNA
<213> ORGANISM: Sorghum halepense

<400> SEQUENCE: 44
acacagcagg tgcaaacttg gcatcaaatg gacggggca ttgagctgga gtggtctatg        60
caacaaagca tccctccagc ctcctgaaag tggagtatgt aagttgaatg acaaaaagag      120
gcctcaaaat aacccaccgc catcctccgg agctactaac cgtaccatgg atgtgatgtt      180
tgccagcagc aaatctcgtg ttgttgctcg tgttttggta gagcacctgc tgctgccgac      240
gatgcaaggt ttctgatcct gtgtgggatc gtctaaccat gggctgattg gttggcgatg      300
gaccccacca gaagtgctgt cggtggaatg gagctattct ccgtttcatt tggactttgt      360
tacctttcac aggatataaa tttatttaag ttgatgcccg tcgtggtatg actagagacg      420
c                                                                      421

<210> SEQ ID NO 45
<211> LENGTH: 507
<212> TYPE: DNA
<213> ORGANISM: Sorghum halepense

<400> SEQUENCE: 45
gcacgagccg ctgcttttga ggtatcaggt gagaagtttt ggagactgcc actggaggag       60
agctactggg aatctatgaa gtccggcgtg gctgatatgg tcaacactgg tggtaggcag      120
ggaggttcta ttaccgctgc cctgttcctg aaacagtttg ttgacgagaa ggtccagtgg      180
atgcacatcg acatggccgg gccagtgtgg aacgacaaga gcgggctgc caccggcttc       240 ggcgtttcga ccctggtgga gtgggtcctc aagaactcct cgtcatgaac aaaacccctt      300
cggccctccc ccacatgtta catgcttttc caagctgcca gcggtgaaga aggtggaga       360 gggtttacca tgttttttc cccctttgt gctaccattc cattccacag ttgcagcctg       420
caaactgcag acccgcctct tggcatgcca agtgggcgtg tgtgataccg ttgtgataga      480
ataatcatca taaagggttt ggacttc                                          507

<210> SEQ ID NO 46
<211> LENGTH: 378
<212> TYPE: DNA
<213> ORGANISM: Sorghum halepense

<400> SEQUENCE: 46
ttagttgtgt caccctgtca catggcggcg cgctggtccc atggcagcac gcccggcatg       60
gcggcggcat ataggtcagc tgcttttcg tggactcgtc gtcgcggttc ggcaaggttc       120
acgttgtgtc gtactcctac taagctacgt ggcgcggtgg gccctcaag acctgttgt        180 gttgtgttgt gttgtgtcgt gtcgtgacaa ataatgtacc agtgtgttat tacttctgtg      240
tcgggttaat ggccccagtg tcggtgctaa tgtggcctgg cttttacaaca catcggttgg     300 gccggggctc tatgtcgttt aaatatgttg gttaatacgt gtcccgtccc atctagtatg      360
```

```
tgtttttgag cgtgtagt                                                  378

<210> SEQ ID NO 47
<211> LENGTH: 133
<212> TYPE: DNA
<213> ORGANISM: Sorghum halepense

<400> SEQUENCE: 47
gcacgagtta tggacagtct tgtacttcca gaattgagtt ttcagtcggt tttgttttgt    60
aaagctcgtt catgcagtca tcgcgtggag ttattataat aaagtggtct gattaacggg   120
aaaaaaaaaa aaa                                                      133

<210> SEQ ID NO 48
<211> LENGTH: 20
<212> TYPE: DNA
<213> ORGANISM: Artificial Sequence
<220> FEATURE:
<223> OTHER INFORMATION: Primer/probe

<400> SEQUENCE: 48
aatcaagcca ttggttcctg                                                20

<210> SEQ ID NO 49
<211> LENGTH: 20
<212> TYPE: DNA
<213> ORGANISM: Artificial Sequence
<220> FEATURE:
<223> OTHER INFORMATION: Primer/probe

<400> SEQUENCE: 49
aagccaagga agaggtggat                                                20

<210> SEQ ID NO 50
<211> LENGTH: 20
<212> TYPE: DNA
<213> ORGANISM: Artificial Sequence
<220> FEATURE:
<223> OTHER INFORMATION: Primer/probe

<400> SEQUENCE: 50
gggatggaca tggtgaaatc                                                20

<210> SEQ ID NO 51
<211> LENGTH: 20
<212> TYPE: DNA
<213> ORGANISM: Artificial Sequence
<220> FEATURE:
<223> OTHER INFORMATION: Primer/probe

<400> SEQUENCE: 51
gaagtcgatg acgaccacct                                                20

<210> SEQ ID NO 52
<211> LENGTH: 20
<212> TYPE: DNA
<213> ORGANISM: Artificial Sequence
<220> FEATURE:
<223> OTHER INFORMATION: Primer/probe

<400> SEQUENCE: 52
gatggatggt gacacagcac                                                20

<210> SEQ ID NO 53
<211> LENGTH: 20
```

```
<212> TYPE: DNA
<213> ORGANISM: Artificial Sequence
<220> FEATURE:
<223> OTHER INFORMATION: Primer/probe

<400> SEQUENCE: 53
ttgagtcagc cagtcagtcg                                               20

<210> SEQ ID NO 54
<211> LENGTH: 20
<212> TYPE: DNA
<213> ORGANISM: Artificial Sequence
<220> FEATURE:
<223> OTHER INFORMATION: Primer/probe

<400> SEQUENCE: 54
ataaaaacgg cctccttgct                                               20

<210> SEQ ID NO 55
<211> LENGTH: 20
<212> TYPE: DNA
<213> ORGANISM: Artificial Sequence
<220> FEATURE:
<223> OTHER INFORMATION: Primer/probe

<400> SEQUENCE: 55
tgctcttcac acaaccaagc                                               20

<210> SEQ ID NO 56
<211> LENGTH: 20
<212> TYPE: DNA
<213> ORGANISM: Artificial Sequence
<220> FEATURE:
<223> OTHER INFORMATION: Primer/probe

<400> SEQUENCE: 56
gcgaggtcga gaagatgaag                                               20

<210> SEQ ID NO 57
<211> LENGTH: 20
<212> TYPE: DNA
<213> ORGANISM: Artificial Sequence
<220> FEATURE:
<223> OTHER INFORMATION: Primer/probe

<400> SEQUENCE: 57
tggatcagtt ggtcttgcag                                               20

<210> SEQ ID NO 58
<211> LENGTH: 20
<212> TYPE: DNA
<213> ORGANISM: Artificial Sequence
<220> FEATURE:
<223> OTHER INFORMATION: Primer/probe

<400> SEQUENCE: 58
tccgtcaact tccacctttc                                               20

<210> SEQ ID NO 59
<211> LENGTH: 20
<212> TYPE: DNA
<213> ORGANISM: Artificial Sequence
<220> FEATURE:
<223> OTHER INFORMATION: Primer/probe

<400> SEQUENCE: 59
```

```
agggttgact cagggaggtt                                               20

<210> SEQ ID NO 60
<211> LENGTH: 20
<212> TYPE: DNA
<213> ORGANISM: Artificial Sequence
<220> FEATURE:
<223> OTHER INFORMATION: Primer/probe

<400> SEQUENCE: 60
ccagcgatag tgcacacatt                                               20

<210> SEQ ID NO 61
<211> LENGTH: 20
<212> TYPE: DNA
<213> ORGANISM: Artificial Sequence
<220> FEATURE:
<223> OTHER INFORMATION: Primer/probe

<400> SEQUENCE: 61
ctctctctcg cgctctgtct                                               20

<210> SEQ ID NO 62
<211> LENGTH: 20
<212> TYPE: DNA
<213> ORGANISM: Artificial Sequence
<220> FEATURE:
<223> OTHER INFORMATION: Primer/probe

<400> SEQUENCE: 62
ctaacctcac cgctttaggg                                               20

<210> SEQ ID NO 63
<211> LENGTH: 19
<212> TYPE: DNA
<213> ORGANISM: Artificial Sequence
<220> FEATURE:
<223> OTHER INFORMATION: Primer/probe

<400> SEQUENCE: 63
ccagcgggag agagaaaaa                                                19

<210> SEQ ID NO 64
<211> LENGTH: 20
<212> TYPE: DNA
<213> ORGANISM: Artificial Sequence
<220> FEATURE:
<223> OTHER INFORMATION: Primer/probe

<400> SEQUENCE: 64
gagtgcgttc agaggttcaa                                               20

<210> SEQ ID NO 65
<211> LENGTH: 20
<212> TYPE: DNA
<213> ORGANISM: Artificial Sequence
<220> FEATURE:
<223> OTHER INFORMATION: Primer/probe

<400> SEQUENCE: 65
cttgactggg tttgccattg                                               20

<210> SEQ ID NO 66
<211> LENGTH: 20
<212> TYPE: DNA
<213> ORGANISM: Artificial Sequence
```

```
<220> FEATURE:
<223> OTHER INFORMATION: Primer/probe

<400> SEQUENCE: 66
tgtgaaattc catggcaaaa                                              20

<210> SEQ ID NO 67
<211> LENGTH: 20
<212> TYPE: DNA
<213> ORGANISM: Artificial Sequence
<220> FEATURE:
<223> OTHER INFORMATION: Primer/probe

<400> SEQUENCE: 67
ataggctccg agtgctacga                                              20

<210> SEQ ID NO 68
<211> LENGTH: 20
<212> TYPE: DNA
<213> ORGANISM: Artificial Sequence
<220> FEATURE:
<223> OTHER INFORMATION: Primer/probe

<400> SEQUENCE: 68
tgaatgatga aggcaatgga                                              20

<210> SEQ ID NO 69
<211> LENGTH: 20
<212> TYPE: DNA
<213> ORGANISM: Artificial Sequence
<220> FEATURE:
<223> OTHER INFORMATION: Primer/probe

<400> SEQUENCE: 69
tgcattcggg actttacaca                                              20

<210> SEQ ID NO 70
<211> LENGTH: 20
<212> TYPE: DNA
<213> ORGANISM: Artificial Sequence
<220> FEATURE:
<223> OTHER INFORMATION: Primer/probe

<400> SEQUENCE: 70
cattggtttt gcgtatcgtg                                              20

<210> SEQ ID NO 71
<211> LENGTH: 20
<212> TYPE: DNA
<213> ORGANISM: Artificial Sequence
<220> FEATURE:
<223> OTHER INFORMATION: Primer/probe

<400> SEQUENCE: 71
gaccgaccgt ctttaaccaa                                              20

<210> SEQ ID NO 72
<211> LENGTH: 20
<212> TYPE: DNA
<213> ORGANISM: Artificial Sequence
<220> FEATURE:
<223> OTHER INFORMATION: Primer/probe

<400> SEQUENCE: 72
tgaatgatga aggcaatgga                                              20
```

```
<210> SEQ ID NO 73
<211> LENGTH: 20
<212> TYPE: DNA
<213> ORGANISM: Artificial Sequence
<220> FEATURE:
<223> OTHER INFORMATION: Primer/probe

<400> SEQUENCE: 73
agagccgttg atgagcctaa                                              20

<210> SEQ ID NO 74
<211> LENGTH: 20
<212> TYPE: DNA
<213> ORGANISM: Artificial Sequence
<220> FEATURE:
<223> OTHER INFORMATION: Primer/probe

<400> SEQUENCE: 74
gggctgtgtc catgatcttt                                              20

<210> SEQ ID NO 75
<211> LENGTH: 20
<212> TYPE: DNA
<213> ORGANISM: Artificial Sequence
<220> FEATURE:
<223> OTHER INFORMATION: Primer/probe

<400> SEQUENCE: 75
agggcatcca gacaaacaac                                              20

<210> SEQ ID NO 76
<211> LENGTH: 20
<212> TYPE: DNA
<213> ORGANISM: Artificial Sequence
<220> FEATURE:
<223> OTHER INFORMATION: Primer/probe

<400> SEQUENCE: 76
gatgttggct tcaccgtttt                                              20

<210> SEQ ID NO 77
<211> LENGTH: 20
<212> TYPE: DNA
<213> ORGANISM: Artificial Sequence
<220> FEATURE:
<223> OTHER INFORMATION: Primer/probe

<400> SEQUENCE: 77
tatttcgcag gacgaccttt                                              20

<210> SEQ ID NO 78
<211> LENGTH: 20
<212> TYPE: DNA
<213> ORGANISM: Artificial Sequence
<220> FEATURE:
<223> OTHER INFORMATION: Primer/probe

<400> SEQUENCE: 78
gcacgagcca cctatctgtc                                              20

<210> SEQ ID NO 79
<211> LENGTH: 20
<212> TYPE: DNA
<213> ORGANISM: Artificial Sequence
<220> FEATURE:
<223> OTHER INFORMATION: Primer/probe
```

```
<400> SEQUENCE: 79
agagggcacg gtgaggttag                                               20

<210> SEQ ID NO 80
<211> LENGTH: 20
<212> TYPE: DNA
<213> ORGANISM: Artificial Sequence
<220> FEATURE:
<223> OTHER INFORMATION: Primer/probe

<400> SEQUENCE: 80
gtcgacgaat tccagtagcc                                               20

<210> SEQ ID NO 81
<211> LENGTH: 20
<212> TYPE: DNA
<213> ORGANISM: Artificial Sequence
<220> FEATURE:
<223> OTHER INFORMATION: Primer/probe

<400> SEQUENCE: 81
gcaagcttga agtgggaact                                               20

<210> SEQ ID NO 82
<211> LENGTH: 20
<212> TYPE: DNA
<213> ORGANISM: Artificial Sequence
<220> FEATURE:
<223> OTHER INFORMATION: Primer/probe

<400> SEQUENCE: 82
atgcaccact gatttggtga                                               20

<210> SEQ ID NO 83
<211> LENGTH: 21
<212> TYPE: DNA
<213> ORGANISM: Artificial Sequence
<220> FEATURE:
<223> OTHER INFORMATION: Primer/probe

<400> SEQUENCE: 83
ttcacaacca gtgaccacaa a                                             21

<210> SEQ ID NO 84
<211> LENGTH: 20
<212> TYPE: DNA
<213> ORGANISM: Artificial Sequence
<220> FEATURE:
<223> OTHER INFORMATION: Primer/probe

<400> SEQUENCE: 84
tagctgctac cacgcacact                                               20

<210> SEQ ID NO 85
<211> LENGTH: 20
<212> TYPE: DNA
<213> ORGANISM: Artificial Sequence
<220> FEATURE:
<223> OTHER INFORMATION: Primer/probe

<400> SEQUENCE: 85
ggccttgtac gttgttggac                                               20

<210> SEQ ID NO 86
```

```
<211> LENGTH: 20
<212> TYPE: DNA
<213> ORGANISM: Artificial Sequence
<220> FEATURE:
<223> OTHER INFORMATION: Primer/probe

<400> SEQUENCE: 86
ttttatgccc acacctccat                                                   20

<210> SEQ ID NO 87
<211> LENGTH: 20
<212> TYPE: DNA
<213> ORGANISM: Artificial Sequence
<220> FEATURE:
<223> OTHER INFORMATION: Primer/probe

<400> SEQUENCE: 87
gtgtggcgta cttcagacca                                                   20

<210> SEQ ID NO 88
<211> LENGTH: 20
<212> TYPE: DNA
<213> ORGANISM: Artificial Sequence
<220> FEATURE:
<223> OTHER INFORMATION: Primer/probe

<400> SEQUENCE: 88
atctgtatgg gaaccgtgct                                                   20

<210> SEQ ID NO 89
<211> LENGTH: 20
<212> TYPE: DNA
<213> ORGANISM: Artificial Sequence
<220> FEATURE:
<223> OTHER INFORMATION: Primer/probe

<400> SEQUENCE: 89
tgtcttggag gggtggttag                                                   20

<210> SEQ ID NO 90
<211> LENGTH: 20
<212> TYPE: DNA
<213> ORGANISM: Artificial Sequence
<220> FEATURE:
<223> OTHER INFORMATION: Primer/probe

<400> SEQUENCE: 90
tgcacgttgc ttcctttgta                                                   20

<210> SEQ ID NO 91
<211> LENGTH: 20
<212> TYPE: DNA
<213> ORGANISM: Artificial Sequence
<220> FEATURE:
<223> OTHER INFORMATION: Primer/probe

<400> SEQUENCE: 91
agagtgctcg gtcactcaca                                                   20

<210> SEQ ID NO 92
<211> LENGTH: 20
<212> TYPE: DNA
<213> ORGANISM: Artificial Sequence
<220> FEATURE:
<223> OTHER INFORMATION: Primer/probe

<400> SEQUENCE: 92
```
tttgggctcc acatgtcata                                           20

<210> SEQ ID NO 93
<211> LENGTH: 20
<212> TYPE: DNA
<213> ORGANISM: Artificial Sequence
<220> FEATURE:
<223> OTHER INFORMATION: Primer/probe

<400> SEQUENCE: 93
gtacggggat gttttggttg                                           20

<210> SEQ ID NO 94
<211> LENGTH: 20
<212> TYPE: DNA
<213> ORGANISM: Artificial Sequence
<220> FEATURE:
<223> OTHER INFORMATION: Primer/probe

<400> SEQUENCE: 94
ggtgattagc ccgttttca                                            20

<210> SEQ ID NO 95
<211> LENGTH: 20
<212> TYPE: DNA
<213> ORGANISM: Artificial Sequence
<220> FEATURE:
<223> OTHER INFORMATION: Primer/probe

<400> SEQUENCE: 95
ataagatgcg cccatagcac                                           20

<210> SEQ ID NO 96
<211> LENGTH: 20
<212> TYPE: DNA
<213> ORGANISM: Artificial Sequence
<220> FEATURE:
<223> OTHER INFORMATION: Primer/probe

<400> SEQUENCE: 96
gcacagccaa agcatacaga                                           20

<210> SEQ ID NO 97
<211> LENGTH: 20
<212> TYPE: DNA
<213> ORGANISM: Artificial Sequence
<220> FEATURE:
<223> OTHER INFORMATION: Primer/probe

<400> SEQUENCE: 97
aatgggccca ctgataacaa                                           20

<210> SEQ ID NO 98
<211> LENGTH: 20
<212> TYPE: DNA
<213> ORGANISM: Artificial Sequence
<220> FEATURE:
<223> OTHER INFORMATION: Primer/probe

<400> SEQUENCE: 98
agctgagggg gagatagacc                                           20

<210> SEQ ID NO 99
<211> LENGTH: 20
<212> TYPE: DNA

```
<213> ORGANISM: Artificial Sequence
<220> FEATURE:
<223> OTHER INFORMATION: Primer/probe

<400> SEQUENCE: 99
aaattctgcc caccagattg                                              20

<210> SEQ ID NO 100
<211> LENGTH: 20
<212> TYPE: DNA
<213> ORGANISM: Artificial Sequence
<220> FEATURE:
<223> OTHER INFORMATION: Primer/probe

<400> SEQUENCE: 100
accagcgaga agagccacta                                              20

<210> SEQ ID NO 101
<211> LENGTH: 20
<212> TYPE: DNA
<213> ORGANISM: Artificial Sequence
<220> FEATURE:
<223> OTHER INFORMATION: Primer/probe

<400> SEQUENCE: 101
gtggatggtg aaggagtcgt                                              20

<210> SEQ ID NO 102
<211> LENGTH: 20
<212> TYPE: DNA
<213> ORGANISM: Artificial Sequence
<220> FEATURE:
<223> OTHER INFORMATION: Primer/probe

<400> SEQUENCE: 102
cctcgcactt gtgctcatta                                              20

<210> SEQ ID NO 103
<211> LENGTH: 20
<212> TYPE: DNA
<213> ORGANISM: Artificial Sequence
<220> FEATURE:
<223> OTHER INFORMATION: Primer/probe

<400> SEQUENCE: 103
tgtgcaatga agccatgttt                                              20

<210> SEQ ID NO 104
<211> LENGTH: 20
<212> TYPE: DNA
<213> ORGANISM: Artificial Sequence
<220> FEATURE:
<223> OTHER INFORMATION: Primer/probe

<400> SEQUENCE: 104
tccctgtgac actgcaagag                                              20

<210> SEQ ID NO 105
<211> LENGTH: 20
<212> TYPE: DNA
<213> ORGANISM: Artificial Sequence
<220> FEATURE:
<223> OTHER INFORMATION: Primer/probe

<400> SEQUENCE: 105
ccccggactt caacagtcta                                              20
```

<210> SEQ ID NO 106
<211> LENGTH: 20
<212> TYPE: DNA
<213> ORGANISM: Artificial Sequence
<220> FEATURE:
<223> OTHER INFORMATION: Primer/probe

<400> SEQUENCE: 106
tgacagccac tcgagaacag                                               20

<210> SEQ ID NO 107
<211> LENGTH: 20
<212> TYPE: DNA
<213> ORGANISM: Artificial Sequence
<220> FEATURE:
<223> OTHER INFORMATION: Primer/probe

<400> SEQUENCE: 107
gccaacaatc acagcaatgt                                               20

<210> SEQ ID NO 108
<211> LENGTH: 20
<212> TYPE: DNA
<213> ORGANISM: Artificial Sequence
<220> FEATURE:
<223> OTHER INFORMATION: Primer/probe

<400> SEQUENCE: 108
acagggtgac tggaatggag                                               20

<210> SEQ ID NO 109
<211> LENGTH: 20
<212> TYPE: DNA
<213> ORGANISM: Artificial Sequence
<220> FEATURE:
<223> OTHER INFORMATION: Primer/probe

<400> SEQUENCE: 109
aggcattctg gtgtctgtcc                                               20

<210> SEQ ID NO 110
<211> LENGTH: 20
<212> TYPE: DNA
<213> ORGANISM: Artificial Sequence
<220> FEATURE:
<223> OTHER INFORMATION: Primer/probe

<400> SEQUENCE: 110
gatcaagggg agatcgtcaa                                               20

<210> SEQ ID NO 111
<211> LENGTH: 20
<212> TYPE: DNA
<213> ORGANISM: Artificial Sequence
<220> FEATURE:
<223> OTHER INFORMATION: Primer/probe

<400> SEQUENCE: 111
ccgatgcctt gaaaatgact                                               20

<210> SEQ ID NO 112
<211> LENGTH: 20
<212> TYPE: DNA
<213> ORGANISM: Artificial Sequence
<220> FEATURE:

```
<223> OTHER INFORMATION: Primer/probe

<400> SEQUENCE: 112
ctgacacatg tcctggttgg                                                      20

<210> SEQ ID NO 113
<211> LENGTH: 20
<212> TYPE: DNA
<213> ORGANISM: Artificial Sequence
<220> FEATURE:
<223> OTHER INFORMATION: Primer/probe

<400> SEQUENCE: 113
atggcatcaa gatcctctgg                                                      20

<210> SEQ ID NO 114
<211> LENGTH: 20
<212> TYPE: DNA
<213> ORGANISM: Artificial Sequence
<220> FEATURE:
<223> OTHER INFORMATION: Primer/probe

<400> SEQUENCE: 114
attttgcgca tggatatggt                                                      20

<210> SEQ ID NO 115
<211> LENGTH: 20
<212> TYPE: DNA
<213> ORGANISM: Artificial Sequence
<220> FEATURE:
<223> OTHER INFORMATION: Primer/probe

<400> SEQUENCE: 115
gacggtgagg cctgttatgt                                                      20

<210> SEQ ID NO 116
<211> LENGTH: 20
<212> TYPE: DNA
<213> ORGANISM: Artificial Sequence
<220> FEATURE:
<223> OTHER INFORMATION: Primer/probe

<400> SEQUENCE: 116
gaagttttcc gccttcctct                                                      20

<210> SEQ ID NO 117
<211> LENGTH: 20
<212> TYPE: DNA
<213> ORGANISM: Artificial Sequence
<220> FEATURE:
<223> OTHER INFORMATION: Primer/probe

<400> SEQUENCE: 117
ttgccaaact gcttcacaag                                                      20

<210> SEQ ID NO 118
<211> LENGTH: 20
<212> TYPE: DNA
<213> ORGANISM: Artificial Sequence
<220> FEATURE:
<223> OTHER INFORMATION: Primer/probe

<400> SEQUENCE: 118
ctgtcaccgg agaagaggag                                                      20
```

```
<210> SEQ ID NO 119
<211> LENGTH: 20
<212> TYPE: DNA
<213> ORGANISM: Artificial Sequence
<220> FEATURE:
<223> OTHER INFORMATION: Primer/probe

<400> SEQUENCE: 119
ggaggtcgaa gagagtgacg                                               20

<210> SEQ ID NO 120
<211> LENGTH: 20
<212> TYPE: DNA
<213> ORGANISM: Artificial Sequence
<220> FEATURE:
<223> OTHER INFORMATION: Primer/probe

<400> SEQUENCE: 120
ctcgacaggg gagttctcag                                               20

<210> SEQ ID NO 121
<211> LENGTH: 20
<212> TYPE: DNA
<213> ORGANISM: Artificial Sequence
<220> FEATURE:
<223> OTHER INFORMATION: Primer/probe

<400> SEQUENCE: 121
cggccaactc attatctcgt                                               20

<210> SEQ ID NO 122
<211> LENGTH: 20
<212> TYPE: DNA
<213> ORGANISM: Artificial Sequence
<220> FEATURE:
<223> OTHER INFORMATION: Primer/probe

<400> SEQUENCE: 122
gcacgaggct aacacaaaca                                               20

<210> SEQ ID NO 123
<211> LENGTH: 20
<212> TYPE: DNA
<213> ORGANISM: Artificial Sequence
<220> FEATURE:
<223> OTHER INFORMATION: Primer/probe

<400> SEQUENCE: 123
gacaacattc tccgcttggt                                               20

<210> SEQ ID NO 124
<211> LENGTH: 20
<212> TYPE: DNA
<213> ORGANISM: Artificial Sequence
<220> FEATURE:
<223> OTHER INFORMATION: Primer/probe

<400> SEQUENCE: 124
ttgttcatca aggcagcaag                                               20

<210> SEQ ID NO 125
<211> LENGTH: 20
<212> TYPE: DNA
<213> ORGANISM: Artificial Sequence
<220> FEATURE:
<223> OTHER INFORMATION: Primer/probe
```

```
<400> SEQUENCE: 125
cgcagtcgac atggtttatg                                              20

<210> SEQ ID NO 126
<211> LENGTH: 20
<212> TYPE: DNA
<213> ORGANISM: Artificial Sequence
<220> FEATURE:
<223> OTHER INFORMATION: Primer/probe

<400> SEQUENCE: 126
cttaattggc agggtgcagt                                              20

<210> SEQ ID NO 127
<211> LENGTH: 20
<212> TYPE: DNA
<213> ORGANISM: Artificial Sequence
<220> FEATURE:
<223> OTHER INFORMATION: Primer/probe

<400> SEQUENCE: 127
gacatctaca acgccgtcct                                              20

<210> SEQ ID NO 128
<211> LENGTH: 20
<212> TYPE: DNA
<213> ORGANISM: Artificial Sequence
<220> FEATURE:
<223> OTHER INFORMATION: Primer/probe

<400> SEQUENCE: 128
ataagttggc attggcttcg                                              20

<210> SEQ ID NO 129
<211> LENGTH: 20
<212> TYPE: DNA
<213> ORGANISM: Artificial Sequence
<220> FEATURE:
<223> OTHER INFORMATION: Primer/probe

<400> SEQUENCE: 129
cagcgaactc aacaatgcac                                              20

<210> SEQ ID NO 130
<211> LENGTH: 20
<212> TYPE: DNA
<213> ORGANISM: Artificial Sequence
<220> FEATURE:
<223> OTHER INFORMATION: Primer/probe

<400> SEQUENCE: 130
ctcgtgttgt tgctcgtgtt                                              20

<210> SEQ ID NO 131
<211> LENGTH: 20
<212> TYPE: DNA
<213> ORGANISM: Artificial Sequence
<220> FEATURE:
<223> OTHER INFORMATION: Primer/probe

<400> SEQUENCE: 131
cggagaatag ctccattcca                                              20

<210> SEQ ID NO 132
<211> LENGTH: 20
```

```
<212> TYPE: DNA
<213> ORGANISM: Artificial Sequence
<220> FEATURE:
<223> OTHER INFORMATION: Primer/probe

<400> SEQUENCE: 132
gtggagtggg tcctcaagaa                                               20

<210> SEQ ID NO 133
<211> LENGTH: 20
<212> TYPE: DNA
<213> ORGANISM: Artificial Sequence
<220> FEATURE:
<223> OTHER INFORMATION: Primer/probe

<400> SEQUENCE: 133
gtatcacaca cgcccacttg                                               20

<210> SEQ ID NO 134
<211> LENGTH: 20
<212> TYPE: DNA
<213> ORGANISM: Artificial Sequence
<220> FEATURE:
<223> OTHER INFORMATION: Primer/probe

<400> SEQUENCE: 134
ccctcaagac cctgttgtgt                                               20

<210> SEQ ID NO 135
<211> LENGTH: 20
<212> TYPE: DNA
<213> ORGANISM: Artificial Sequence
<220> FEATURE:
<223> OTHER INFORMATION: Primer/probe

<400> SEQUENCE: 135
gttgtaaagc caggccacat                                               20

<210> SEQ ID NO 136
<211> LENGTH: 20
<212> TYPE: DNA
<213> ORGANISM: Artificial Sequence
<220> FEATURE:
<223> OTHER INFORMATION: Primer/probe

<400> SEQUENCE: 136
caagacatcc agcgtttcct                                               20

<210> SEQ ID NO 137
<211> LENGTH: 20
<212> TYPE: DNA
<213> ORGANISM: Artificial Sequence
<220> FEATURE:
<223> OTHER INFORMATION: Primer/probe

<400> SEQUENCE: 137
gatcgatcga tcgagcaagt                                               20

<210> SEQ ID NO 138
<211> LENGTH: 20
<212> TYPE: DNA
<213> ORGANISM: Artificial Sequence
<220> FEATURE:
<223> OTHER INFORMATION: Primer/probe

<400> SEQUENCE: 138
```

```
tctcaaaggg aaaacgatgg                                                    20

<210> SEQ ID NO 139
<211> LENGTH: 20
<212> TYPE: DNA
<213> ORGANISM: Artificial Sequence
<220> FEATURE:
<223> OTHER INFORMATION: Primer/probe

<400> SEQUENCE: 139
catactgcga gcagaccaac                                                    20

<210> SEQ ID NO 140
<211> LENGTH: 20
<212> TYPE: DNA
<213> ORGANISM: Artificial Sequence
<220> FEATURE:
<223> OTHER INFORMATION: Primer/probe

<400> SEQUENCE: 140
tgtttaggcg aagggaaatg                                                    20
```

DETECTION OF JOHNSONGRASS AND ITS HYBRID SEED

CROSS-REFERENCE

This utility application claims the benefit of U.S. Provisional Application Ser. No. 61/329,271, filed Apr. 29, 2010.

FIELD

The disclosure relates to molecular genetics and more specifically the detection of seed purity through molecular genetics.

BACKGROUND

*Sorghum* is a genus of plants consisting of multiple species of grasses. Some *Sorghum* species are valuable crops, being used for food, animal feed and the production of alcohol and biofuels. For example *Sorghum bicolor*, commonly called sorghum, is one of the most important cereal crops for subsistence farmers in arid and semi-arid portions of Africa, Asia and the Americas. The crop is essential for human life on marginal lands throughout the poorest regions of the world. In developed countries, sorghum is important as a feed crop and as a crop that can be grown on marginal lands as part of a sustainable agroecosystem.

However, other *Sorghum* species are not so useful. For example, *Sorghum halepense*, commonly called Johnsongrass, is classified as an invasive species in the United States. This species is commonly found growing in crop fields and other open areas, such as pastures, and has been known to grow so quickly as to choke out the desired crops planted in farming fields. Another weed species in the *Sorghum* genus is *S. propinquum*. This species is closely related to Johnsongrass but is diploid, larger and has a different geographic distribution. Some studies have also suggested that Johnsongrass is a descendent of *S. propinquum* and possibly an interspecific hybrid descendent of sorghum and *S. propinquum*. (See, e.g., Paterson, et al., (1995) *PNAS* 92:6127; Paterson and Chandler, "Risk of Gene Flow from sorghum to Johnsongrass" (1996), available at http://www.isb.vt.edu/brarg/brasym96/paterson96.htm).

Unfortunately, Johnsongrass and sorghum are able to readily hybridize. While it is possible to phenotypically distinguish a hybrid plant from the cultivar, it is nearly impossible to distinguish between their seeds. This difficulty creates a genetic purity problem in sorghum seed lots. Because of this problem, one needs to be able to assess the level of Johnsongrass contamination in a seed lot to ensure that the seed lot is as pure as required or desired. Presently, such an assessment is commonly done through grow-outs, where 40,000 individual seeds are planted and grown and the number of hybrid plants counted. This solution is labor intensive, time consuming, expensive and inefficient.

Thus, there is a need for an improved method of detecting the presence of and/or quantifying the amount of Johnsongrass seed or Johnsongrass hybrid seed in sorghum seed lots.

SUMMARY

The present disclosure is drawn to methods and compositions for an efficient way of detecting Johnsongrass or its genetic material. One aspect of the present disclosure is a method for detecting the presence or amount of Johnsongrass or Johnsongrass hybrid genetic material in a biological sample, the method comprising detecting the presence or amount of at least a portion of one or more Johnsongrass detection sequences, whereby positive detection indicates the presence or amount of Johnsongrass or Johnsongrass hybrid genetic material in the biological sample.

In certain embodiments, the one or more Johnsongrass detection sequences comprise SEQ ID NOS.: 1-47 or a nucleic acid sequence essentially similar thereto. In certain other embodiments, the detecting step comprises hybridizing an oligonucleotide probe or oligonucleotide primer to at least a portion of the one or more Johnsongrass detection sequences, preferably the oligonucleotide probe or oligonucleotide primer being hybridizable to at least a portion of one or more of SEQ ID NOS.: 1-47. The oligonucleotide primer can comprise one or more of SEQ ID NOS.: 48-135 or nucleic acid sequences essentially similar thereto while the oligonucleotide probe can comprise one or more of SEQ ID NOS.: 136-140 or nucleic acid sequences essentially similar thereto. In still further embodiments, the detecting step further comprises amplifying at least a portion of the one or more Johnsongrass detection sequences or the detecting step comprises (a) hybridizing an oligonucleotide probe to at least a portion of the one or more Johnsongrass detection sequences, wherein the oligonucleotide probe further comprises a detectable label; and (b) detecting the detectable label. Also preferred are methods wherein the oligonucleotide probe is affixed to a solid support, that solid support possibly comprising a microarray.

Another aspect of the present disclosure is a method for detecting the presence or amount of Johnsongrass seed or Johnsongrass hybrid seed in a seed sample, the sample containing nucleic acids, the method comprising:
  (a) providing a reaction mixture comprising primer pairs for amplification of at least a portion of one or more of SEQ ID NOS.: 1-47 or nucleic acid sequences essentially similar thereto;
  (b) subjecting the reaction mixture to a nucleic acid amplification process that will produce an amplification product of the one or more of SEQ ID NOS.: 1-47 or nucleic acid sequences essentially similar thereto if present in the reaction mixture; and
  (c) detecting the one or more amplification products of step (b), whereby a positive detection of amplification indicates the presence or amount of Johnsongrass seed and/or Johnsongrass hybrid seed in the seed sample.

In certain embodiments of the disclosure, the reaction mixture of step (a) comprises primer pairs for amplification of one or more of SEQ ID NOS.: 17, 21, 31, 36 and 37 and nucleic acid sequences essentially similar thereto, preferably the primer pairs including one or more primer pairs selected from the group consisting of SEQ ID NOS.: 76 and 77; SEQ ID NOS.: 84 and 85; SEQ ID NOS.: 104 and 105; SEQ ID NOS.: 114 and 115 and SEQ ID NOS.: 116 and 117. Also preferred are methods wherein the primer pairs include SEQ ID NOS.: 76 and 77, SEQ ID NOS.: 84 and 85, SEQ ID NOS.: 104 and 105, SEQ ID NOS.: 114 and 115 and SEQ ID NOS.: 116 and 117. In certain other embodiments of the disclosure, the reaction mixture of step (a) comprises primers for the nucleic acid region SEQ ID NO.: 17, those primer pairs preferably comprising a first nucleic acid sequence comprising SEQ ID NO.: 76 and a second nucleic acid sequence comprising SEQ ID NO.: 77. In other embodiments, the reaction mixture further comprises a nucleic acid probe for one or more of the nucleic acid regions selected, the nucleic acid probes preferably comprising one or more of SEQ ID NOS.: 136-140 and the nucleic acid probes also preferably comprising a detectable label.

In other aspects, the present disclosure comprises an isolated polynucleotide essentially similar to at least 10 consecutive nucleic acid residues of SEQ ID NOS.: 48-140. In certain aspects, the isolated polynucleotide is at least 90% identical to at least 10 consecutive nucleic acid residues of SEQ ID NOS.: 48-140, preferably at least 93% identical to at least 15 consecutive nucleic acid residues of SEQ ID NOS.: 48-140. In certain embodiments, the isolated polynucleotide further comprises a detectable label.

In still other aspects, the present disclosure comprises a replication composition for use in performance of PCR, comprising (a) one or more primer pairs for amplification of at least a portion of one or more of SEQ ID NOS.: 1-47 and (b) a thermostable DNA polymerase. In certain embodiments, the one or more primer pairs of part (a) comprise primer pairs for amplification of one or more of SEQ ID NOS.: 17, 21, 31 and 36. In other embodiments, the primer pairs comprise one or more of SEQ ID NO.: 76 and SEQ ID NO.: 77; SEQ ID NO.: 84 and SEQ ID NO.: 85; SEQ ID NO.: 104 and SEQ ID NO.: 105; SEQ ID NO.: 114 and SEQ ID NO.: 115; and SEQ ID NO.: 116 and SEQ ID NO.: 117. In other embodiments, the replication composition further comprises a nucleic acid probe for one or more of the primer pairs, the nucleic acid probes selected from the group consisting of SEQ ID NOS.: 136-140.

In yet other aspects, the present disclosure comprises a kit for detection of Johnsongrass DNA in a seed sample, the kit comprising a replication composition of the present disclosure.

SUMMARY OF THE SEQUENCES

SEQ ID NO.: 1 is a nucleotide sequence present in the Johnsongrass sequence database, with a homologous sequence in the *S. propinquum* database, but absent from the sorghum database. SEQ ID NO.: 1 or its reverse complementary sequence contains or is hybridizable with, and can be amplified by the use of SEQ ID NO.: 48 in conjunction with SEQ ID NO.: 49.

SEQ ID NO.: 2 is a nucleotide sequence present in the Johnsongrass sequence database, with a homologous sequence in the *S. propinquum* database, but absent from the sorghum database. SEQ ID NO.: 2 or its reverse complementary sequence contains or is hybridizable with, and can be amplified by the use of complementary sequence contains or is hybridizable with, and can be amplified by the use of SEQ ID NO.: 50 in conjunction with SEQ ID NO.: 51.

SEQ ID NO.: 3 is a nucleotide sequence present in the Johnsongrass sequence database, with a homologous sequence in the *S. propinquum* database, but absent from the sorghum database. SEQ ID NO.: 3 or its reverse complementary sequence contains or is hybridizable with, and can be amplified by the use of SEQ ID NO.: 52 in conjunction with SEQ ID NO.: 53.

SEQ ID NO.: 4 is a nucleotide sequence present in the Johnsongrass sequence database, with a homologous sequence in the *S. propinquum* database, but absent from the sorghum database. SEQ ID NO.: 4 or its reverse complementary sequence contains or is hybridizable with, and can be amplified by the use of SEQ ID NO.: 54 in conjunction with SEQ ID NO.: 55.

SEQ ID NO.: 5 is a nucleotide sequence present in the Johnsongrass sequence database, with a homologous sequence in the *S. propinquum* database, but absent from the sorghum database. SEQ ID NO.:5 or its reverse complementary sequence contains or is hybridizable with, and can be amplified by the use of SEQ ID NO.: 56 in conjunction with SEQ ID NO.: 57.

SEQ ID NO.: 6 is a Johnsongrass expressed sequence tag (EST) nucleotide sequence that is absent from the sorghum and non-redundant nucleotide databases. SEQ ID NO.: 6 or its reverse complementary sequence contains or is hybridizable with and can be amplified by the use of SEQ ID NO.:58 in conjunction with SEQ ID NO.: 59.

SEQ ID NO.: 7 is a Johnsongrass EST nucleotide sequence that is absent from the sorghum and non-redundant nucleotide databases.

SEQ ID NO.: 8 is a Johnsongrass EST nucleotide sequence that is absent from the sorghum and non-redundant nucleotide databases.

SEQ ID NO.: 9 is a Johnsongrass EST nucleotide sequence that is absent from the sorghum and non-redundant nucleotide databases. SEQ ID NO.: 9 or its reverse complementary sequence contains or is hybridizable with, and can be amplified by the use of SEQ ID NO.: 60 in conjunction with SEQ ID NO.: 61.

SEQ ID NO.: 10 is a Johnsongrass EST nucleotide sequence that is absent from the sorghum and non-redundant nucleotide databases. SEQ ID NO.: 10 or its reverse complementary sequence contains or is hybridizable with, and can be amplified by the use of SEQ ID NO.: 62 in conjunction with SEQ ID NO.: 63.

SEQ ID NO.: 11 is a Johnsongrass EST nucleotide sequence that is absent from the sorghum and non-redundant nucleotide databases. SEQ ID NO.: 11 or its reverse complementary sequence contains or is hybridizable with, and can be amplified by the use of SEQ ID NO.: 64 in conjunction with SEQ ID NO.: 65.

SEQ ID NO.: 12 is a Johnsongrass EST nucleotide sequence that is absent from the sorghum and non-redundant nucleotide databases. SEQ ID NO.: 12 or its reverse complementary sequence contains or is hybridizable with, and can be amplified by the use of SEQ ID NO.: 66 in conjunction with SEQ ID NO.: 67.

SEQ ID NO.: 13 is a Johnsongrass EST nucleotide sequence that is absent from the sorghum and non-redundant nucleotide databases. SEQ ID NO.: 13 or its reverse complementary sequence contains or is hybridizable with, and can be amplified by the use of SEQ ID NO.: 68 in conjunction with SEQ ID NO.: 69.

SEQ ID NO.: 14 is a Johnsongrass EST nucleotide sequence that is absent from the sorghum and non-redundant nucleotide databases. SEQ ID NO.: 14 or its reverse complementary sequence contains or is hybridizable with, and can be amplified by the use of SEQ ID NO.: 70 in conjunction with SEQ ID NO.: 71.

SEQ ID NO.: 15 is a Johnsongrass EST nucleotide sequence that is absent from the sorghum and non-redundant nucleotide databases. SEQ ID NO.: 15 or its reverse complementary sequence contains or is hybridizable with, and can be amplified by the use of SEQ ID NO.: 72 in conjunction with SEQ ID NO.: 73.

SEQ ID NO.: 16 is a Johnsongrass EST nucleotide sequence that is absent from the sorghum and non-redundant nucleotide databases. SEQ ID NO.: 16 or its reverse complementary sequence contains or is hybridizable with, and can be amplified by the use of SEQ ID NO.: 74 in conjunction with SEQ ID NO.: 75.

SEQ ID NO.: 17 is a Johnsongrass EST nucleotide sequence that is absent from the sorghum and non-redundant nucleotide databases. SEQ ID NO.: 17 or its reverse complementary sequence contains or is hybridizable with, and can be amplified by the use of SEQ ID NO.: 76 in conjunction with SEQ ID NO.: 77, and also contains a binding site for probe SEQ ID NO.: 136.

SEQ ID NO.: 18 is a Johnsongrass EST nucleotide sequence that is absent from the sorghum and non-redundant nucleotide databases. SEQ ID NO.: 18 or its reverse complementary sequence contains or is hybridizable with, and can be amplified by the use of SEQ ID NO.: 78 in conjunction with SEQ ID NO.: 79.

SEQ ID NO.: 19 is a Johnsongrass EST nucleotide sequence that is absent from the sorghum and non-redundant nucleotide databases. SEQ ID NO.: 19 or its reverse complementary sequence contains or is hybridizable with, and can be amplified by the use of SEQ ID NO.: 80 in conjunction with SEQ ID NO.: 81.

SEQ ID NO.: 20 is an *S. propinquum* marker nucleotide sequence that is absent from the sorghum and non-redundant nucleotide databases. SEQ ID NO.: 20 or its reverse complementary sequence contains or is hybridizable with, and can be amplified by the use of SEQ ID NO.: 82 in conjunction with SEQ ID NO.: 83.

SEQ ID NO.: 21 is an *S. propinquum* marker nucleotide sequence that is absent from the sorghum and non-redundant nucleotide databases. SEQ ID NO.: 21 or its reverse complementary sequence contains or is hybridizable with, and can be amplified by the use of SEQ ID NO.: 84 in conjunction with SEQ ID NO.: 85, and also contains a binding site for probe SEQ ID NO.: 137.

SEQ ID NO.: 22 is an *S. propinquum* marker nucleotide sequence that is absent from the sorghum and non-redundant nucleotide databases. SEQ ID NO.: 22 or its reverse complementary sequence contains or is hybridizable with, and can be amplified by the use of SEQ ID NO.: 86 in conjunction with SEQ ID NO.: 87.

SEQ ID NO.: 23 is an *S. propinquum* marker nucleotide sequence that is absent from the sorghum and non-redundant nucleotide databases. SEQ ID NO.: 23 or its reverse complementary sequence contains or is hybridizable with, and can be amplified by the use of SEQ ID NO.: 88 in conjunction with SEQ ID NO.: 89.

SEQ ID NO.: 24 is an *S. propinquum* marker nucleotide sequence that is absent from the sorghum and non-redundant nucleotide databases. SEQ ID NO.: 24 or its reverse complementary sequence contains or is hybridizable with, and can be amplified by the use of SEQ ID NO.: 90 in conjunction with SEQ ID NO.: 91.

SEQ ID NO.: 25 is an *S. propinquum* marker nucleotide sequence that is absent from the sorghum and non-redundant nucleotide databases. SEQ ID NO.: 25 or its reverse complementary sequence contains or is hybridizable with, and can be amplified by the use of SEQ ID NO.: 92 in conjunction with SEQ ID NO.: 93.

SEQ ID NO.: 26 is an *S. propinquum* marker nucleotide sequence that is absent from the sorghum and non-redundant nucleotide databases. SEQ ID NO.: 26 or its reverse complementary sequence contains or is hybridizable with, and can be amplified by the use of SEQ ID NO.: 94 in conjunction with SEQ ID NO.: 95.

SEQ ID NO.: 27 is an *S. propinquum* marker nucleotide sequence that is absent from the sorghum and non-redundant nucleotide databases. SEQ ID NO.: 27 or its reverse complementary sequence contains or is hybridizable with, and can be amplified by the use of SEQ ID NO.: 96 in conjunction with SEQ ID NO.: 97.

SEQ ID NO.: 28 is an *S. propinquum* marker nucleotide sequence that is absent from the sorghum and non-redundant nucleotide databases. SEQ ID NO.: 28 or its reverse complementary sequence contains or is hybridizable with, and can be amplified by the use of SEQ ID NO.: 98 in conjunction with SEQ ID NO.: 99.

SEQ ID NO.: 29 is an *S. propinquum* marker nucleotide sequence that is absent from the sorghum and non-redundant nucleotide databases. SEQ ID NO.: 29 or its reverse complementary sequence contains or is hybridizable with, and can be amplified by the use of SEQ ID NO.: 100 in conjunction with SEQ ID NO.: 101.

SEQ ID NO.: 30 is an *S. propinquum* marker nucleotide sequence that is absent from the sorghum and non-redundant nucleotide databases. SEQ ID NO.: 30 or its reverse complementary sequence contains or is hybridizable with, and can be amplified by the use of SEQ ID NO.: 102 in conjunction with SEQ ID NO.: 103.

SEQ ID NO.: 31 is an *S. propinquum* marker nucleotide sequence that is absent from the sorghum and non-redundant nucleotide databases. SEQ ID NO.: 31 or its reverse complementary sequence contains or is hybridizable with, and can be amplified by the use of SEQ ID NO.: 104 in conjunction with SEQ ID NO.: 105, and also contains a binding site for probe SEQ ID NO.: 138.

SEQ ID NO.: 32 is an *S. propinquum* marker nucleotide sequence that is absent from the sorghum and non-redundant nucleotide databases. SEQ ID NO.: 32 or its reverse complementary sequence contains or is hybridizable with, and can be amplified by the use of SEQ ID NO.: 106 in conjunction with SEQ ID NO.: 107.

SEQ ID NO.: 33 is an *S. propinquum* marker nucleotide sequence that is absent from the sorghum and non-redundant nucleotide databases. SEQ ID NO.: 33 or its reverse complementary sequence contains or is hybridizable with, and can be amplified by the use of SEQ ID NO.: 108 in conjunction with SEQ ID NO.: 109.

SEQ ID NO.: 34 is an *S. propinquum* marker nucleotide sequence that is absent from the sorghum and non-redundant nucleotide databases. SEQ ID NO.: 34 or its reverse complementary sequence contains or is hybridizable with, and can be amplified by the use of SEQ ID NO.: 110 in conjunction with SEQ ID NO.: 111.

SEQ ID NO.: 35 is an *S. propinquum* marker nucleotide sequence that is absent from the sorghum and non-redundant nucleotide databases. SEQ ID NO.: 35 or its reverse complementary sequence contains or is hybridizable with, and can be amplified by the use of SEQ ID NO.: 112 in conjunction with SEQ ID NO.: 113.

SEQ ID NO.: 36 is an *S. propinquum* marker nucleotide sequence that is absent from the sorghum and non-redundant nucleotide databases. SEQ ID NO.: 36 or its reverse complementary sequence contains or is hybridizable with, and can be amplified by the use of SEQ ID NO.: 114 in conjunction with SEQ ID NO.: 115, and also contains a binding site for probe SEQ ID NO.: 139.

SEQ ID NO.: 37 is an *S. propinquum* marker nucleotide sequence that is absent from the sorghum and non-redundant nucleotide databases. SEQ ID NO.: 37 or its reverse complementary sequence contains or is hybridizable with, and can be amplified by the use of SEQ ID NO.: 116 in conjunction with SEQ ID NO.: 117, and also contains a binding site for probe SEQ ID NO.: 140.

SEQ ID NO.: 38 is an *S. propinquum* marker nucleotide sequence that is absent from the sorghum and non-redundant nucleotide databases. SEQ ID NO.: 38 or its reverse complementary sequence contains or is hybridizable with, and can be amplified by the use of SEQ ID NO.: 118 in conjunction with SEQ ID NO.: 119 or SEQ ID NO.: 120 in conjunction with SEQ ID NO.: 121.

SEQ ID NO.: 39 is an *S. propinquum* marker nucleotide sequence that is absent from the sorghum and non-redundant nucleotide databases.

SEQ ID NO.: 40 is an *S. propinquum* marker nucleotide sequence that is absent from the sorghum and non-redundant nucleotide databases. SEQ ID NO.: 40 or its reverse complementary sequence contains or is hybridizable with, and can be amplified by the use of SEQ ID NO.: 122 in conjunction with SEQ ID NO.: 123.

SEQ ID NO.: 41 is a nucleotide sequence present in the Johnsongrass sequence database, with a homologous sequence in the *S. propinquum* database, but absent from the sorghum database. SEQ ID NO.: 41 or its reverse complementary sequence contains or is hybridizable with, and can be amplified by the use of SEQ ID NO.: 124 in conjunction with SEQ ID NO.: 125.

SEQ ID NO.: 42 is a nucleotide sequence present in the Johnsongrass sequence database, with a homologous sequence in the *S. propinquum* database, but absent from the sorghum database. SEQ ID NO.: 42 or its reverse complementary sequence contains or is hybridizable with, and can be amplified by the use of SEQ ID NO.: 126 in conjunction with SEQ ID NO.: 127.

SEQ ID NO.: 43 is a nucleotide sequence present in the Johnsongrass sequence database, with a homologous sequence in the *S. propinquum* database, but absent from the sorghum database. SEQ ID NO.: 43 or its reverse complementary sequence contains or is hybridizable with, and can be amplified by the use of SEQ ID NO.: 128 in conjunction with SEQ ID NO.: 129.

SEQ ID NO.: 44 is a nucleotide sequence present in the Johnsongrass sequence database, with a homologous sequence in the *S. propinquum* database, but absent from the sorghum database. SEQ ID NO.: 44 or its reverse complementary sequence contains or is hybridizable with, and can be amplified by the use of SEQ ID NO.: 130 in conjunction with SEQ ID NO.: 131.

SEQ ID NO.: 45 is a nucleotide sequence present in the Johnsongrass sequence database, with a homologous sequence in the *S. propinquum* database, but absent from the sorghum database. SEQ ID NO.: 45 or its reverse complementary sequence contains or is hybridizable with, and can be amplified by the use of SEQ ID NO.: 132 in conjunction with SEQ ID NO.: 133.

SEQ ID NO.: 46 is a nucleotide sequence present in the Johnsongrass sequence database, with a homologous sequence in the *S. propinquum* database, but absent from the sorghum database. SEQ ID NO.: 46 or its reverse complementary sequence contains or is hybridizable with, and can be amplified by the use of SEQ ID NO.: 134 in conjunction with SEQ ID NO.: 135.

SEQ ID NO.: 47 is a nucleotide sequence present in the Johnsongrass sequence database, with a homologous sequence in the *S. propinquum* database, but absent from the sorghum database.

SEQ ID NOS.: 48 and 49 are the nucleotide sequences of regions of the Johnsongrass genome, each capable of being used as a probe or primer, either alone or in combination, in detection of the presence of SEQ ID NO.: 1 or its complementary sequence and the subsequent detection of the presence of Johnsongrass.

SEQ ID NOS.: 50 and 51 are the nucleotide sequences of regions of the Johnsongrass genome, each capable of being used as a probe or primer, either alone or in combination, in detection of the presence of SEQ ID NO.: 2 or its complementary sequence and the subsequent detection of the presence of Johnsongrass.

SEQ ID NOS.: 52 and 53 are the nucleotide sequences of regions of the Johnsongrass genome, each capable of being used as a probe or primer, either alone or in combination, in detection of the presence of SEQ ID NO.: 3 or its complementary sequence and the subsequent detection of the presence of Johnsongrass.

SEQ ID NOS.: 54 and 55 are the nucleotide sequences of regions of the Johnsongrass genome, each capable of being used as a probe or primer, either alone or in combination, in detection of the presence of SEQ ID NO.: 4 or its complementary sequence and the subsequent detection of the presence of Johnsongrass.

SEQ ID NOS.: 56 and 57 are the nucleotide sequences of regions of the Johnsongrass genome, each capable of being used as a probe or primer, either alone or in combination, in detection of the presence of SEQ ID NO.: 5 or its complementary sequence and the subsequent detection of the presence of Johnsongrass.

SEQ ID NOS.: 58 and 59 are the nucleotide sequences of regions of the Johnsongrass genome, each capable of being used as a probe or primer, either alone or in combination, in detection of the presence of SEQ ID NO.: 6 or its complementary sequence and the subsequent detection of the presence of Johnsongrass.

SEQ ID NOS.: 60 and 61 are the nucleotide sequences of regions of the Johnsongrass genome, each capable of being used as a probe or primer, either alone or in combination, in detection of the presence of SEQ ID NO.: 9 or its complementary sequence and the subsequent detection of the presence of Johnsongrass.

SEQ ID NOS.: 62 and 63 are the nucleotide sequences of regions of the Johnsongrass genome, each capable of being used as a probe or primer, either alone or in combination, in detection of the presence of SEQ ID NO.: 10 or its complementary sequence and the subsequent detection of the presence of Johnsongrass.

SEQ ID NOS.: 64 and 65 are the nucleotide sequences of regions of the Johnsongrass genome, each capable of being used as a probe or primer, either alone or in combination, in detection of the presence of SEQ ID NO.: 11 or its complementary sequence and the subsequent detection of the presence of Johnsongrass.

SEQ ID NOS.: 66 and 67 are the nucleotide sequences of regions of the Johnsongrass genome, each capable of being used as a probe or primer, either alone or in combination, in detection of the presence of SEQ ID NO.: 12 or its complementary sequence and the subsequent detection of the presence of Johnsongrass.

SEQ ID NOS.: 68 and 69 are the nucleotide sequences of regions of the Johnsongrass genome, each capable of being used as a probe or primer, either alone or in combination, in detection of the presence of SEQ ID NO.: 13 or its complementary sequence and the subsequent detection of the presence of Johnsongrass.

SEQ ID NOS.: 70 and 71 are the nucleotide sequences of regions of the Johnsongrass genome, each capable of being used as a probe or primer, either alone or in combination, in detection of the presence of SEQ ID NO.: 14 or its complementary sequence and the subsequent detection of the presence of Johnsongrass.

SEQ ID NOS.: 72 and 73 are the nucleotide sequences of regions of the Johnsongrass genome, each capable of being used as a probe or primer, either alone or in combination, in detection of the presence of SEQ ID NO.: 15 or its complementary sequence and the subsequent detection of the presence of Johnsongrass.

SEQ ID NOS.: 74 and 75 are the nucleotide sequences of regions of the Johnsongrass genome, each capable of being used as a probe or primer, either alone or in combination, in detection of the presence of SEQ ID NO.: 16 or its complementary sequence and the subsequent detection of the presence of Johnsongrass.

SEQ ID NOS.: 76 and 77 are the nucleotide sequences of regions of the Johnsongrass genome, each capable of being used as a probe or primer, either alone or in combination, in detection of the presence of SEQ ID NO.: 17 or its complementary sequence and the subsequent detection of the presence of Johnsongrass.

SEQ ID NOS.: 78 and 79 are the nucleotide sequences of regions of the Johnsongrass genome, each capable of being used as a probe or primer, either alone or in combination, in detection of the presence of SEQ ID NO.: 18 or its complementary sequence and the subsequent detection of the presence of Johnsongrass.

SEQ ID NOS.: 80 and 81 are the nucleotide sequences of regions of the Johnsongrass genome, each capable of being used as a probe or primer, either alone or in combination, in detection of the presence of SEQ ID NO.: 19 or its complementary sequence and the subsequent detection of the presence of Johnsongrass.

SEQ ID NOS.: 82 and 83 are the nucleotide sequences of regions of the Johnsongrass genome, each capable of being used as a probe or primer, either alone or in combination, in detection of the presence of SEQ ID NO.: 20 or its complementary sequence and the subsequent detection of the presence of Johnsongrass.

SEQ ID NOS.: 84 and 85 are the nucleotide sequences of regions of the Johnsongrass genome, each capable of being used as a probe or primer, either alone or in combination, in detection of the presence of SEQ ID NO.: 21 or its complementary sequence and the subsequent detection of the presence of Johnsongrass.

SEQ ID NOS.: 86 and 87 are the nucleotide sequences of regions of the Johnsongrass genome, each capable of being used as a probe or primer, either alone or in combination, in detection of the presence of SEQ ID NO.: 22 or its complementary sequence and the subsequent detection of the presence of Johnsongrass.

SEQ ID NOS.: 88 and 89 are the nucleotide sequences of regions of the Johnsongrass genome, each capable of being used as a probe or primer, either alone or in combination, in detection of the presence of SEQ ID NO.: 23 or its complementary sequence and the subsequent detection of the presence of Johnsongrass.

SEQ ID NOS.: 90 and 91 are the nucleotide sequences of regions of the Johnsongrass genome, each capable of being used as a probe or primer, either alone or in combination, in detection of the presence of SEQ ID NO.: 24 or its complementary sequence and the subsequent detection of the presence of Johnsongrass.

SEQ ID NOS.: 92 and 93 are the nucleotide sequences of regions of the Johnsongrass genome, each capable of being used as a probe or primer, either alone or in combination, in detection of the presence of SEQ ID NO.: 25 or its complementary sequence and the subsequent detection of the presence of Johnsongrass.

SEQ ID NOS.: 94 and 95 are the nucleotide sequences of regions of the Johnsongrass genome, each capable of being used as a probe or primer, either alone or in combination, in detection of the presence of SEQ ID NO.: 26 or its complementary sequence and the subsequent detection of the presence of Johnsongrass.

SEQ ID NOS.: 96 and 97 are the nucleotide sequences of regions of the Johnsongrass genome, each capable of being used as a probe or primer, either alone or in combination, in detection of the presence of SEQ ID NO.: 27 or its complementary sequence and the subsequent detection of the presence of Johnsongrass.

SEQ ID NOS.: 98 and 99 are the nucleotide sequences of regions of the Johnsongrass genome, each capable of being used as a probe or primer, either alone or in combination, in detection of the presence of SEQ ID NO.: 28 or its complementary sequence and the subsequent detection of the presence of Johnsongrass.

SEQ ID NOS.: 100 and 101 are the nucleotide sequences of regions of the Johnsongrass genome, each capable of being used as a probe or primer, either alone or in combination, in detection of the presence of SEQ ID NO.: 29 or its complementary sequence and the subsequent detection of the presence of Johnsongrass.

SEQ ID NOS.: 102 and 103 are the nucleotide sequences of regions of the Johnsongrass genome, each capable of being used as a probe or primer, either alone or in combination, in detection of the presence of SEQ ID NO.: 30 or its complementary sequence and the subsequent detection of the presence of Johnsongrass.

SEQ ID NOS.: 104 and 105 are the nucleotide sequences of regions of the Johnsongrass genome, each capable of being used as a probe or primer, either alone or in combination, in detection of the presence of SEQ ID NO.: 31 or its complementary sequence and the subsequent detection of the presence of Johnsongrass.

SEQ ID NOS.: 106 and 107 are the nucleotide sequences of regions of the Johnsongrass genome, each capable of being used as a probe or primer, either alone or in combination, in detection of the presence of SEQ ID NO.: 32 or its complementary sequence and the subsequent detection of the presence of Johnsongrass.

SEQ ID NOS.: 108 and 109 are the nucleotide sequences of regions of the Johnsongrass genome, each capable of being used as a probe or primer, either alone or in combination, in detection of the presence of SEQ ID NO.: 33 or its complementary sequence and the subsequent detection of the presence of Johnsongrass.

SEQ ID NOS.: 110 and 111 are the nucleotide sequences of regions of the Johnsongrass genome, each capable of being used as a probe or primer, either alone or in combination, in detection of the presence of SEQ ID NO.: 34 or its complementary sequence and the subsequent detection of the presence of Johnsongrass.

SEQ ID NOS.: 112 and 113 are the nucleotide sequences of regions of the Johnsongrass genome, each capable of being used as a probe or primer, either alone or in combination, in detection of the presence of SEQ ID NO.: 35 or its complementary sequence and the subsequent detection of the presence of Johnsongrass.

SEQ ID NOS.: 114 and 115 are the nucleotide sequences of regions of the Johnsongrass genome, each capable of being used as a probe or primer, either alone or in combination, in detection of the presence of SEQ ID NO.: 36 or its complementary sequence and the subsequent detection of the presence of Johnsongrass.

SEQ ID NOS.: 116 and 117 are the nucleotide sequences of regions of the Johnsongrass genome, each capable of being used as a probe or primer, either alone or in combination, in detection of the presence of SEQ ID NO.: 37 or its complementary sequence and the subsequent detection of the presence of Johnsongrass.

SEQ ID NOS.: 118, 119, 120 and 121 are the nucleotide sequences of regions of the Johnsongrass genome, each capable of being used as a probe or primer, either alone or in combination, in detection of the presence of SEQ ID NO.: 38 or its complementary sequence and the subsequent detection of the presence of Johnsongrass.

SEQ ID NOS.: 122 and 123 are the nucleotide sequences of regions of the Johnsongrass genome, each capable of being used as a probe or primer, either alone or in combination, in detection of the presence of SEQ ID NO.: 40 or its complementary sequence and the subsequent detection of the presence of Johnsongrass.

SEQ ID NOS.: 124 and 125 are the nucleotide sequences of regions of the Johnsongrass genome, each capable of being used as a probe or primer, either alone or in combination, in detection of the presence of SEQ ID NO.: 41 or its complementary sequence and the subsequent detection of the presence of Johnsongrass.

SEQ ID NOS.: 126 and 127 are the nucleotide sequences of regions of the Johnsongrass genome, each capable of being used as a probe or primer, either alone or in combination, in detection of the presence of SEQ ID NO.: 42 or its complementary sequence and the subsequent detection of the presence of Johnsongrass.

SEQ ID NOS.: 128 and 129 are the nucleotide sequences of regions of the Johnsongrass genome, each capable of being used as a probe or primer, either alone or in combination, in detection of the presence of SEQ ID NO.: 43 or its complementary sequence and the subsequent detection of the presence of Johnsongrass.

SEQ ID NOS.: 130 and 131 are the nucleotide sequences of regions of the Johnsongrass genome, each capable of being used as a probe or primer, either alone or in combination, in detection of the presence of SEQ ID NO.: 44 or its complementary sequence and the subsequent detection of the presence of Johnsongrass.

SEQ ID NOS.: 132 and 133 are the nucleotide sequences of regions of the Johnsongrass genome, each capable of being used as a probe or primer, either alone or in combination, in detection of the presence of SEQ ID NO.: 45 or its complementary sequence and the subsequent detection of the presence of Johnsongrass.

SEQ ID NOS.: 134 and 135 are the nucleotide sequences of regions of the Johnsongrass genome, each capable of being used as a probe or primer, either alone or in combination, in detection of the presence of SEQ ID NO.: 46 or its complementary sequence and the subsequent detection of the presence of Johnsongrass.

SEQ ID NO.: 136 is the nucleotide sequence of a region of the Johnsongrass genome capable of being used as a probe or primer in detection of the presence of SEQ ID NO.: 17 and subsequent detection of the presence of Johnsongrass. This sequence is preferably used as a probe that will hybridize to and allow detection of SEQ ID NO.: 17.

SEQ ID NO.: 137 is the nucleotide sequence of a region of the Johnsongrass genome capable of being used as a probe or primer in detection of the presence of SEQ ID NO.: 21 and subsequent detection of the presence of Johnsongrass. This sequence is preferably used as a probe that will hybridize to and allow detection of SEQ ID NO.: 21.

SEQ ID NO.: 138 is the nucleotide sequence of a region of the Johnsongrass genome capable of being used as a probe or primer in detection of the presence of SEQ ID NO.: 31 and subsequent detection of the presence of Johnsongrass. This sequence is preferably used as a probe that will hybridize to and allow detection of SEQ ID NO.: 31.

SEQ ID NO.: 139 is the nucleotide sequence of a region of the Johnsongrass genome capable of being used as a probe or primer in detection of the presence of SEQ ID NO.: 36 and subsequent detection of the presence of Johnsongrass. This sequence is preferably used as a probe that will hybridize to and allow detection of SEQ ID NO.: 36.

SEQ ID NO.: 140 is the nucleotide sequence of a region of the Johnsongrass genome capable of being used as a probe or primer in detection of the presence of SEQ ID NO.: 37 and subsequent detection of the presence of Johnsongrass. This sequence is preferably used as a probe that will hybridize to and allow detection of SEQ ID NO.: 37.

The sequences conform with 37 C.F.R. §§1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis) and Section 208 and Annex C of the Administrative Instructions). The symbols and format used for nucleotide sequence data comply with the rules set forth in 37 C.F.R. §1.822.

DETAILED DESCRIPTION

The present disclosure relates in part to methods for identifying and/or quantifying Johnsongrass and/or Johnsongrass hybrid genetic material in biological samples, which methods are based on nucleic acid sequences present in Johnsongrass. In particular, methods are provided for identifying and/or quantifying Johnsongrass seed and/or Johnsongrass hybrid seed in seed samples. In one particular embodiment, the methods comprise amplifying a sequence of a nucleic acid using a polymerase chain reaction with at least two primers. In other embodiments, the methods comprise detection through the use of detectably labeled oligonucleotide probes or microarrays. Primers and probes useful for detecting nucleic acid sequences present in Johnsongrass are also provided.

Selective detection of Johnsongrass genetic material in biological sample is provided. The primers, probes, nucleotide sequences provided herein enable selective and specific detection of Johnsongrass genetic material including DNA, RNA from other closely related species. The selective and specific detection methods disclosed herein also enable quantifying the presence and the amount of Johnsongrass genetic material including Johnsongrass hybrid material in a biological sample. For example, the methods disclosed herein provide seed purity determination for sorghum samples.

The present disclosure further relates in part to certain specific nucleotide sequences present in Johnsongrass that are described herein, which can be used to develop specific identification methods for detecting Johnsongrass and/or Johnsongrass hybrid genetic material in biological samples. The disclosure also relates in part to replication compositions and kits useful for identifying Johnsongrass in biological samples, the kits comprising one or more oligonucleotide primers or probes that specifically recognize the specific Johnsongrass nucleotide sequences described herein.

The entire contents of all references cited in this disclosure are specifically incorporated by reference herein. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

The terms "consisting essentially of" generally means e.g., the specified nucleic acid sequence and those that do not materially affect the basic and material characteristics of the specified nucleic acid sequence. Similarly, components or steps that do not materially affect the basic and material characteristics of the claimed invention are encompassed by the term "consisting essentially of".

The term "sorghum" refers to *Sorghum bicolor*. The term "Johnsongrass" refers to *Sorghum halepense*. The term "Johnsongrass hybrid" refers to a plant or portion thereof, such as a seed that contains genetic elements from both Johnsongrass and another species, especially a species from the *Sorghum* genus. An example of a Johnsongrass hybrid is a seed that results from a cross of sorghum and Johnsongrass.

Selectively discriminates generally refers to the ability of the probes and primers disclosed herein to preferentially bind or hybridize to a genetic material of Johnsongrass or its hybrid compared to binding to genetic material from a related species, e.g., *Sorghum bicolor*.

As used herein, a biological sample is any sample that contains biological material, including a sample of a seed, more than one seed, a plant, plant material or products comprising plant material. The term "plant" is intended to encompass plant tissue at any stage of maturity, as well as any cells, tissues or organs taken from or derived from any such plant, including, without limitation, any seeds, leaves, stems, flowers, roots, single cells, gametes, cell cultures, tissue cultures or protoplasts. "Plant material", as used herein refers to material which is obtained or derived from a plant. It is to be understood that, in the context of the present disclosure, such biological samples are tested for the presence of nucleic acids, and, therefore, such samples comprise nucleic acids.

The term "Johnsongrass detection sequence" refers to a nucleic acid sequence which has been found to be present in one or more strains of Johnsongrass and/or *Sorghum propinquum*, but partially or completely absent from, or of relatively low homology in one or more strains of sorghum.

The terms "polynucleotide", "polynucleotide sequence", "nucleic acid sequence", "nucleic acid fragment" and "oligonucleotide" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more strands of cDNA, genomic DNA, synthetic DNA or mixtures thereof.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Polymerase chain reaction" is abbreviated PCR. "Ligase chain reaction" is abbreviated LCR. "Strand displacement amplification" is abbreviated SDA.

The term "amplification" refers to synthesis of multiple copies of a nucleic acid sequence through a primer-directed reaction, such as PCR, LCR or SDR. The term "amplification product" refers to nucleic acid fragments produced during a primer-directed amplification reaction. The term "replication composition" refers to a composition that contains the elements necessary to perform some form of nucleic acid replication or amplification. If PCR methodology is selected, the replication composition may comprise, for example, nucleotide triphosphates, two (or more) primers with appropriate sequences, thermostable polymerase, buffers, solutes and proteins. These reagents and details describing procedures for their use in amplifying nucleic acids are provided, for example, in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., Thermus aquaticus ligase), two sets of adjacent oligonucleotides (wherein one member of each set is complementary to each of the target strands), Tris-HCl buffer, KCl, EDTA, NAD, dithiothreitol and salmon sperm DNA. See, for example, Tabor, et al., (1985) *Proc. Natl. Acad. Sci. USA* 82:1074-1078.

The term "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label.

A probe can either be an independent entity or complexed with or otherwise attached to a primer, such as where a probe is connected via its 3' terminus to a primer's 5' terminus through a linker, which may be a nucleotide or non-nucleotide linker and which may be a non-amplifiable linker, such as a hexethylene glycol (HEG) or 18-carbon linker. In such a case, this would be termed a "primer-probe complex." One example of such a probe-primer complex can be found in U.S. Pat. No. 6,326,145, incorporated herein by reference in its entirety, which are frequently referred to as "Scorpion probes" or "Scorpion primers."

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin or haptens) and the like. A detectable label can also include a combination of a reporter and a quencher.

The term "reporter" refers to a substance or a portion thereof that is capable of exhibiting a detectable signal, which signal can be suppressed by a quencher. The detectable signal of the reporter is, for example, fluorescence in the detectable range. The term "quencher" refers to a substance or portion thereof that is capable of suppressing, reducing, inhibiting, etc., the detectable signal produced by the reporter.

As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Preferably, the reporter may be selected from fluorescent organic dyes modified with a suitable linking group for attachment to the oligonucleotide, such as to the terminal 3' carbon or terminal 5' carbon. The quencher may also be selected from organic dyes, which may or may not be fluorescent, depending on the embodiment of the present disclosure. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radioactively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, In: Handbook of Fluorescence Spectra of Aromatic Molecules, 2nd ed., Academic Press, New York, 1971, the content of which is incorporated herein by reference.

Preferred reporter-quencher pairs may be selected from xanthene dyes including fluoresceins and rhodamine dyes. Particularly preferred reporters may be selected from dyes such as SYBR green, 5-carboxyfluorescein (5-FAM™ available from Applied Biosystems of Foster City in Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7, 7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems and the like. Other preferred fluorescent compounds for use as reporters are the naphthylamines, having an amino group in the alpha or beta position. Included among such naphthylamino compounds are 1-demethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isoth iocyanatoacridine; N-(p-(2-benzoxazolyl)phenyl)maleimide; benzoxadiazoles; stilbenes; pyrenes and the like.

Particularly preferred quenchers may be selected from 6-carboxy-tetramethyl-rhodamine, 4-(4-dimethylaminophenylazo)benzoic acid (DABYL), tetramethylrhodamine (TAMRA), BHQ-0™ BHQ-1 ™, BHQ-2™ and BHQ-3™, each of which are available from Biosearch Technologies, Inc. of Novato in Calif., QSY-7™, QSY-9™, QSY21™ and QSY35™, each of which are available from Molecular Probes, Inc. and the like.

One preferred example of a probe that contains a reporter and a quencher is a probe that is to be used in a 5'-exonuclease assay, such as the Taqman® real-time PCR technique. In this context, the oligonucleotide probe will have a reporter attached at or near its 5' or 3' end and a quencher attached at or near the other end such that the quencher is able to quench any fluorescence of the reporter. The probe will also contain sufficient number of phosphodiester linkages adjacent to its 5' end so that the 5' to 3' nuclease activity employed during the amplification reaction can efficiently degrade the bound probe to separate the reporters and quenchers, thereby allowing the reporter to fluoresce.

Yet another example of a probe that contains a reporter and quencher is a Molecular Beacon type probe, which contains a probe region flanked by self-complementary regions that allow the probe to form a stem-loop structure when unbound from the probe's target sequence. Such probes typically have a reporter attached at or near one terminus and a quencher attached at or near the other terminus such that the quencher is in sufficiently close proximity to the reporter to cause quenching when the probe is in its unbound, and thus stem-loop, form.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide or peptide nucleic acid units. The term "non-participatory" refers to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993) and *Current Protocols in Molecular Biology*, Chapter 2, Ausubel, et al., Eds., Greene Publishing and Wiley-Interscience, New York (1995). Hybridization and/or wash conditions can be applied for at least 10, 30, 60, 90, 120 or 240 minutes.

For hybridizations with shorter nucleic acids, i.e., oligonucleotides, the position of mismatches becomes more important and the length of the oligonucleotide determines its specificity (see, Sambrook, et al., supra, 11.7-11.8). In one preferred embodiment the length for a hybridizable nucleic acid, i.e., an oligonucleotide primer or probe, is at least about 10 consecutive nucleotides. In other embodiments a preferred minimum length for a hybridizable nucleic acid is at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides; at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 70 nucleotides, at least about 80 nucleotides, at least about 90 nucleotides, at least about 100 nucleotides, at least about 120 nucleotides, at least about 140 nucleotides, at least about 160 nucleotides, at least about 180 nucleotides or at least about 200 nucleotides. The nucleotides mentioned herein may be substantially consecutive. Furthermore, the skilled artisan will recognize that the temperature and wash solution salt concentration may be adjusted as necessary according to factors such as length of the probe.

As used herein, "sequence identity" with regard to nucleotide sequences (DNA or RNA), refers to the number of positions with identical nucleotides divided by the number of nucleotides in the shorter of the two sequences. The alignment of the two nucleotide sequences can be performed, for example, by the Wilbur and Lipmann algorithm (Wilbur and Lipmann, (1983) *Proc. Natl. Acad. Sci. USA* 80:726) using a window-size of 20 nucleotides, a word length of 4 nucleotides and a gap penalty of 4. Computer-assisted analysis and interpretation of sequence data, including sequence alignment as described above, can, e.g., be conveniently performed using the programs of the Intelligenetics™ Suite (Intelligenetics Inc., Calif.) or the sequence analysis software package of the Genetics Computer Group (GCG, University of Wisconsin Biotechnology center). Sequences are indicated as "essentially similar" when they have a sequence identity of at least about 75%, particularly at least about 80%, more particularly at least about 85%, still more particularly about 90%, even more particularly about 91%, still more particularly about 92%, even more particularly about 93%, still more particularly about 94%, even more particularly about 95%, still more particularly about 96%, even more particularly about 97%, still more particularly about 98%, even more particularly about 99%, and especially about 100%. When RNA sequences are said to be essentially similar or have a certain degree of sequence identity with DNA sequences, thymidine (T) in the DNA sequence is considered equal to uracil (U) in the RNA sequence. "Complementary to" as used herein refers to the complementarity between the A and T(U), and G and C nucleotides in nucleotide sequences.

A "kit" as used herein refers to a set of reagents for the purpose of performing the method of the disclosure, more particularly, the identification of Johnsongrass in biological samples. A preferred embodiment of the kit of the disclosure comprises at least one or two specific primers, as described above. Optionally, the kit can further comprise any other reagent described herein in the PCR protocol. Alternatively, according to another embodiment of this disclosure, the kit can comprise a specific probe, as described above, which specifically hybridizes with nucleic acids of biological samples to identify the presence of Johnsongrass. Optionally, the kit can further comprise any other reagent (such as but not limited to hybridizing buffer or label) for identification of Johnsongrass in biological samples, using the specific probe.

Standard recombinant DNA and molecular cloning techniques used herein are well known in the art and are described by, for example, Sambrook, et al., supra and by Ausubel, et al., *Current Protocols in Molecular Biology*, published by Greene Publishing Assoc. and Wiley-Interscience (1987). Standard PCR protocols are described in the art, such as in "PCR Applications Manual" (Roche Molecular Biochemicals, 2nd Edition, 1999). It is understood, however, that a number of parameters in the PCR protocol may need to be adjusted to specific laboratory conditions and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR protocol. These adjustments will, however, be apparent to a person skilled in the art and are furthermore detailed in current PCR application manuals such as the one cited above.

Johnsongrass Detection Sequences

As discussed above, Johnsongrass is closely related to sorghum and is likely an interspecific hybrid of sorghum and *S. propinquum*. Methods and compositions disclosed herein provide detection of Johnsongrass or Johnsongrass hybrid material, even in a background of sorghum, through the detection of the presence of one or more Johnsongrass detection sequences or nucleic acid sequences present in one or more varieties of Johnsongrass and/or *S. propinquum* but absent from or of relatively low homology in one or more varieties of sorghum.

Identification of appropriate Johnsongrass detection sequences can be achieved through in silico analysis and comparison of databases of sorghum, Johnsongrass, and *S. propinquum* nucleic acid sequences. Examples of suitable Johnsongrass detection sequences include SEQ ID NOS.:1-47 and nucleic acid sequences essentially similar thereto. In particular, nucleic acid sequences 75% identical, 80% identical, 85% identical, 90% identical, 91% identical, 92% identical, 93% identical, 94% identical, 95% identical, 96% identical, 97% identical, 98% identical, 99% identical or 100% identical to SEQ ID NOS.: 1-47 or a portion thereof are useful in the present disclosure.

Following the determination of appropriate Johnsongrass detection sequences, detection of Johnsongrass according to the present disclosure can be accomplished by any method capable of positively detecting the presence of one or more Johnsongrass detection sequences, or some portion thereof, in a biological sample. Importantly, the detection method need not detect the entire Johnsongrass detection sequence, but rather only needs to be directed toward a portion of sufficient length to positively identify the desired Johnsongrass detection sequence. To that end, detection will preferably be directed toward a portion of the Johnsongrass detection sequence at least about 10 nucleic acids in length, at least about 11 nucleic acids in length, at least about 12 nucleic acids in length, at least about 13 nucleic acids in length, at least about 14 nucleic acids in length, at least about 15 nucleic acids in length, at least about 16 nucleic acids in length, at least about 17 nucleic acids in length, at least about 18 nucleic acids in length, at least about 19 nucleic acids in length, at least about 20 nucleic acids in length, at least about 21 nucleic acids in length, at least about 22 nucleic acids in length, at least about 23 nucleic acids in length, at least about 24 nucleic acids in length, at least about 25 nucleic acids in length, at least about 26 nucleic acids in length, at least about 27 nucleic acids in length, at least about 28 nucleic acids in length, at least about 29 nucleic acids in length, at least about 30 nucleic acids in length, at least about 35 nucleic acids in length, at least about 40 nucleic acids in length, at least about 45 nucleic acids in length, at least about 50 nucleic acids in length, at least about 55 nucleic acids in length, at least about 60 nucleic acids in length, at least about 65 nucleic acids in length, at least about 70 nucleic acids in length, at least about 75 nucleic acids in length, at least about 80 nucleic acids in length, at least about 85 nucleic acids in length, at least about 90 nucleic acids in length, at least about 95 nucleic acids in length, at least about 100 nucleic acids in length, at least about 110 nucleic acids in length, at least about 120 nucleic acids in length, at least about 130 nucleic acids in length, at least about 140 nucleic acids in length, at least about 150 nucleic acids in length, at least about 160 nucleic acids in length, at least about 170 nucleic acids in length, at least about 180 nucleic acids in length, at least about 190 nucleic acids in length, at least about 200 nucleic acids in length, at least about 225 nucleic acids in length, at least about 250 nucleic acids in length, at least about 275 nucleic acids in length, at least about 300 nucleic acids in length, at least about 350 nucleic acids in length, at least about 400 nucleic acids in length, at least about 450 nucleic acids in length, at least about 500 nucleic acids in length, at least about 600 nucleic acids in length, at least about 700 nucleic acids in length, at least about 800 nucleic acids in length, at least about 900 nucleic acids in length, at least about 1000 nucleic acids in length or about the full length of the Johnsongrass detection sequence identified.

While examples of suitable methods for detecting these regions are included herein, it is to be understood that the disclosure is not limited to the methods described. Rather any suitable method can be employed to detect these Johnsongrass detection sequences and, subsequently, Johnsongrass or Johnsongrass hybrid material.

Oligonucleotides

Several suitable methods of detecting Johnsongrass detection sequences involve the use of oligonucleotide primers and/or probes. For example, oligonucleotide primers capable of hybridizing to Johnsongrass detection sequences can be employed in a PCR reaction. As discussed above, these primers need not be fully complementary to the target sequence to be hybridizable thereto and thus useful in the present disclosure. The oligonucleotide primers of the present disclosure can also contain a detectable label, for example a 5' end label. SEQ ID NOS.: 48-135 and nucleic acid sequences essentially similar thereto are examples of oligonucleotide primers useful in the present disclosure. In particular, oligonucleotide primers 75% identical, 80% identical, 85% identical, 90% identical, 91% identical, 92% identical, 93% identical, 94% identical, 95% identical, 96% identical, 97% identical, 98% identical, 99% identical or 100% identical to SEQ ID NOS.: 48-135 or a portion thereof are useful in the present disclosure. Further, hybridization using oligonucleotide probes is commonly employed for detection of target sequences and the methodologies are generally known to one skilled in the art. Again, these probes need not be fully complementary to the target sequence to be hybridizable thereto, and thus useful in the present disclosure.

A nucleic acid probe sequence can also optionally be employed with the primer sequence pairs of the present disclosure in an amplification based detection technique, such as in the 3'-exonuclease assay.

Oligonucleotides of the present disclosure could also contain both primer and probe regions, and thus be employed as a primer-probe complex in an appropriate assay, such as a Scorpion probe assay. Such primer-probe complexes commonly contain a non-amplifiable linker that connects the 3' terminus of the probe region to the 5' terminus of the primer region. This non-amplifiable linker stops extension of a complementary strand from proceeding into the probe region of the primer-probe complex. Examples of such non-amplifiable linkages include hexethylene glycol (HEG) and, preferably, 18-carbon linkers. Primer-probe complexes of the present disclosure can also contain a self-complementary region that allows the primer-probe complex to form a stem-loop structure when the probe is unbound from its target DNA, which may be useful, for example, in bringing the reporter and quencher into sufficiently close proximity to one another to cause the reporter signal to be quenched. In some instances, a blocking oligonucleotide can be employed with a primer-probe complex, which blocking oligonucleotide is capable of hybridizing to the probe region of the primer-probe complex when the probe region is unbound from its target DNA. If the reporter is attached to the primer-probe complex and the quencher is attached to the blocking oligonucleotide, this can bring the reporter and quencher into sufficiently close proximity to one another to allow quenching to occur.

Oligonucleotide probes of the present disclosure can also be affixed to a solid support, such as a glass microarray slide.

Assay Methods

Detection of the Johnsongrass detection sequences, and subsequent detection of the presence or amount of Johnsongrass or Johnsongrass generic material, may be accomplished in any suitable manner. Preferred methods are primer-directed amplification methods and nucleic acid hybridization methods.

Primer-Directed Amplification Assay Methods

A variety of primer-directed nucleic acid amplification methods are known in the art which can be employed in the present disclosure, including thermal cycling methods (e.g., PCR, RT-PCR and LCR), as well as isothermal methods and strand displacement amplification (SDA). The preferred method is PCR. In one preferred embodiment, one or more primer pairs selected from SEQ ID NOS.: 48-135 and nucleic acid sequences essentially similar thereto may be used as primers in PCR amplification for the detection of one or more of SEQ ID NOS.: 1-47 and nucleic acid sequences essentially similar thereto.

A skilled person will understand that any generally acceptable thermal cycling conditions may be used for successfully detecting Johnsongrass detection sequences using oligonucleotides of the instant disclosure, and, depending on the sample to be tested and other laboratory conditions, routine optimization for the cycling conditions may be necessary to achieve optimal sensitivity and specificity.

Any suitable nucleic acid replication composition in any format can be used in the present disclosure. A typical replication composition for PCR amplification may comprise, for example, dATP, dCTP, dGTP, dTTP, target specific primers and a suitable polymerase. If the replication composition is in liquid form, suitable buffers known in the art may be used (see, e.g., Sambrook, J., et al., supra). Alternatively, if the replication composition is contained in a tablet form, then typical tabletization reagents may be included, such as stabilizers and binding agents.

A preferred replication composition of the instant disclosure comprises (a) at least one primer pair selected from SEQ ID NOS.: 48-135 and nucleic acid sequences essentially similar thereto, and (b) thermostable DNA polymerase. Another preferred replication composition of the present disclosure comprises (a) one or more primer pairs selected from SEQ ID NOS.: 76 and 77, SEQ ID NOS.: 84 and 85, SEQ ID NOS.: 104 and 105, SEQ ID NOS.: 114 and 115 and SEQ ID NOS.: 116 and 117 and nucleic acid sequences essentially similar thereto and (b) a thermostable DNA polymerase. Yet another preferred composition is a replication composition comprising (a) one or more primer pairs selected from SEQ ID NOS.: 76 and 77, SEQ ID NOS.: 84 and 85, SEQ ID NOS.: 104 and 105, SEQ ID NOS.: 114 and 115, and SEQ ID NOS.: 116 and 117 and nucleic acid sequences essentially similar thereto; (b) a thermostable DNA polymerase and (c) one or more probes selected from SEQ ID NOS.: 136-140 and nucleic acid sequences essentially similar thereto, the probes comprising a detectable label. Preferably the detectable label comprises a reporter capable of emitting a detectable signal and a quencher capable of substantially quenching the reporter and preventing the emission of the detectable signal when the reporter and quencher are in sufficiently close proximity to one another. A preferred kit of the instant disclosure comprises any one of the above replication compositions.

In some instances, an internal positive control can be included in the reaction. The internal positive control can include control template nucleic acids (e.g., DNA or RNA), control primers and control nucleic acid probe. The control reaction is useful to validate the amplification reaction. Amplification of the control DNA occurs within the same reaction tube as the sample that is being tested and therefore indicates a successful amplification reaction when samples are target negative, i.e., no target amplification product is produced. Control DNA will be of appropriate size and base composition to permit amplification in a primer-directed amplification reaction. The control template DNA sequence may be obtained from essentially any source, but must be reproducibly amplified under the same conditions that permit the amplification of the target amplification product.

Primer-directed amplification products of Johnsongrass detection sequences, such as SEQ ID NOS.: 1-47 and nucleic acid sequences essentially similar thereto, can be analyzed using various methods, including both heterogeneous detection methods and homogenous detection methods.

Homogenous detection may be employed to carry out "real-time" primer-directed nucleic acid amplification and detection, using primer pairs of the instant disclosure (e.g., real-time PCR and real-time RT-PCR). Preferred real-time methods are set forth in U.S. Pat. Nos. 6,171,785, 5,994,056, 6,326,145, 5,804,375, 5,538,848, 5,487,972 and 5,210,015, each of which is hereby incorporated by reference in its entirety.

A preferred real-time detection method is the 5'-exonuclease detection method, as set forth in U.S. Pat. Nos. 5,804,375, 5,538,848, 5,487,972 and 5,210,015, each of which is hereby incorporated by reference in its entirety. One example of such a method is the Taqman real time PCR assay. In the 5'-exonuclease detection assay, a modified probe is employed during PCR which binds intermediate to or between the two members of the amplification primer pair.

It should be understood that the present disclosure could be operated using a combination of these techniques, such as by having a Scorpion probe directed to one target region and a Taqman® probe directed to a second target region. It should also be understood that the disclosure is not limited to the above-described techniques. Rather, one skilled in the art would recognize that other techniques for detecting amplification as known in the art could also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporter and quenchers become sufficiently distant from each other. As a result, the quenching is substantially abated causing an increase in the fluorescence emission detected.

Nucleic Acid Hybridization Methods

In addition to primer-directed amplification assay methods, nucleic acid hybridization assay methods can be employed in the present disclosure for detection of Johnsongrass detection sequences. The basic components of a nucleic acid hybridization test include a probe, a sample suspected of containing Johnsongrass material, and a specific hybridization method. Typically, the probe length can vary from as few as 10 bases to the full length of the Johnsongrass detection sequence. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. Examples of probes useful in nucleic acid hybridization methods in the present disclosure are any of SEQ ID NOS.: 48-140 and nucleic acid sequences essentially similar thereto.

Hybridization methods are well known in the art. Typically, the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate or between 0.5-20 mM EDTA, FICOLL (Pharmacia Inc.) (about 300-500 kilodaltons), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA or yeast RNA) and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples suspected of contamination and buffers for the disbursement and lysis of the sample. A second component would include media in either dry or liquid form for the hybridization of target and probe polynucleotides, as well as for the removal of undesirable and nonduplexed forms by washing. A third component includes a solid support (e.g., dipstick) upon which is fixed (or to which is conjugated) unlabeled nucleic acid probe(s) that is (are) complementary to one or more Johnsongrass detection sequences, such as SEQ ID NOS.: 1-47 and nucleic acid sequences essentially similar thereto. A fourth component would contain labeled probe that is complementary to a second and different region of the same DNA strand to which the immobilized, unlabeled nucleic acid probe of the third component is hybridized.

Another preferred nucleic acid hybridization method involves the use of DNA or oligonucleotide microarrays. In this technique, oligonucleotide probes, such as one or more of SEQ ID NOS.: 48-140 and nucleic acid sequences essentially similar thereto, are attached to a solid support, such as a glass slide. Labeled nucleic acids derived from the sample of interest are then hybridized to the oligonucleotides attached to the solid support. Following washing of unbound nucleic acids, the slide is visualized, with a positive detection of label indicating the presence of the target for which each oligonucleotide is directed. In a preferred method, more than one, and preferably all, of the oligonucleotides of SEQ ID NOS.: 48-140 are attached to the solid support such that detection of more than one, and preferably all, of SEQ ID NOS.: 1-47 can be simultaneously monitored and detected.

EXAMPLES

The present disclosure is further defined in the following Examples. It should be understood that these Examples, while indicating preferred embodiments of the disclosure, are given by way of illustration only.

Unless otherwise stated, all recombinant DNA techniques are carried out according to standard protocols as described, for example, in Sambrook, et al., (1989) Molecular Cloning: A Laboratory Manual, Second Edition, Cold Spring Harbor Laboratory Press, NY and in Volumes 1 and 2 of Ausubel, et al., (1994) Current Protocols in Molecular Biology, Current Protocols, USA. Standard materials and methods for plant molecular work are described, for example, in Plant Molecular Biology Labfax (1993) by Croy published by BIOS Scientific Publications Ltd (UK) and Blackwell Scientific Publications, UK.

Example 1

In Silico Identification of Candidate Johnsongrass Detection Sequences

Candidate Johnsongrass detection sequences were identified. To begin the candidate identification process, a database of Johnsongrass and *Sorghum propinquum* sequences was derived. The database consisted of a set of Johnsongrass sequences, consisting of 1965 expressed sequence tags (ESTs) and 191 restriction fragment length polymorphism (RFLP) marker sequences, and a set of *S. propinquum* sequences, consisting of 20,881 ESTs, 23,703 genome survey sequences (GSSs) and 223 marker sequences, all of which were obtained from the genBank database of the National Center for Biotechnology Information (NCBI) (http://www.ncbi.nlm.nih.gov/) as of Nov. 11, 2007.

Each of these sets of sequences was aligned against the public v1.0 release (Sbi1 assembly) of the *Sorghum bicolor* genome (http://genome.jgi-psf.org/Sorbi1/Sorbi1.home.html) using BLASTN (Altschul, et al., 1997) at expected value cutoff of e-10, 70% identity and 70 nt overlap.

Sequences that were found to be present in Johnsongrass and/or *S. propinquum* but absent from the sorghum database were retained and further screened against the NCBI non-redundant nucleotide database (nt) with the above parameters to further identify those sequences likely to be unique to Johnsongrass and *S. propinquum*. The GSSs and ESTs thus identified were then assembled into longer sequences using the PHRAP assembly program (Version 0.990329; http://www.phrap.org/phredphrap/phrap.html) at default parameters. The Johnsongrass and *S. propinquum* sequences were then further aligned against each other with the BLASTN algorithm to identify homologue markers with high specificity. This process identified a set of candidate Johnsongrass detection sequences that were subsequently used for laboratory validation.

Example 2

PCR Validation of Candidate Sequences

Primer Design:

Forty-three of the candidate Johnsongrass detection sequences identified through the in silico analysis of Example 1 were selected for laboratory validation via PCR assays. First, the Primer3 software program was used to design PCR amplification primers for the 43 candidate sequences using the default software settings. Table 1 lists the 44 primer pairs that were designed (one of the Johnsongrass detection sequences had two distinct primer sets designed for it).

TABLE 1

List of primers surveyed

| Primer Set | Target SEQ ID | Target Name | Left (Forward) Primer SEQ ID | Left (Forward) Primer Sequence | Right (Reverse) Primer SEQ ID | Right (Reverse) Primer Sequence |
|---|---|---|---|---|---|---|
| A | 1 | Contig7 | 48 | AATCAAGCCATTGGTTCCTG | 49 | AAGCCAAGGAAGAGGTGGAT |
| B | 2 | Contig39 | 50 | GGGATGGACATGGTGAAATC | 51 | GAAGTCGATGACGACCACCT |
| C | 3 | Contig44 | 52 | GATGGATGGTGACACAGCAC | 53 | TTGAGTCAGCCAGTCAGTCG |
| D | 4 | Contig46 | 54 | ATAAAAACGGCCTCCTTGCT | 55 | TGCTCTTCACACAACCAAGC |
| E | 5 | Contig51 | 56 | GCGAGGTCGAGAAGATGAAG | 57 | TGGATCAGTTGGTCTTGCAG |
| F | 6 | Gr2.1 | 58 | TCCGTCAACTTCCACCTTTC | 59 | AGGGTTGACTCAGGGAGGTT |
| G | 9 | Gr2.4 | 60 | CCAGCGATAGTGCACACATT | 61 | CTCTCTCTCGCGCTCTGTCT |
| H | 10 | Gr2.5 | 62 | CTAACCTCACCGCTTTAGGG | 63 | CCAGCGGGAGAGAGAAAAA |
| I | 11 | Gr2.6 | 64 | GAGTGCGTTCAGAGGTTCAA | 65 | CTTGACTGGGTTTGCCATTG |
| J | 12 | Gr2.7 | 66 | TGTGAAATTCCATGGCAAAA | 67 | ATAGGCTCCGAGTGCTACGA |
| K | 13 | Gr2.8 | 68 | TGAATGATGAAGGCAATGGA | 69 | TGCATTCGGGACTTTACACA |
| L | 14 | Gr2.9 | 70 | CATTGGTTTTGCGTATCGTG | 71 | GACCGACCGTCTTTAACCAA |
| M | 15 | Gr2.10 | 72 | TGAATGATGAAGGCAATGGA | 73 | AGAGCCGTTGATGAGCCTAA |
| N | 16 | Gr2.11 | 74 | GGGCTGTGTCCATGATCTTT | 75 | AGGGCATCCAGACAAACAAC |
| O | 17 | Gr2.12 | 76 | GATGTTGGCTTCACCGTTTT | 77 | TATTTCGCAGGACGACCTTT |
| P | 18 | Gr2.13 | 78 | GCACGAGCCACCTATCTGTC | 79 | AGAGGGCACGGTGAGGTTAG |
| Q | 19 | Gr2.14 | 80 | GTCGACGAATTCCAGTAGCC | 81 | GCAAGCTTGAAGTGGGAACT |
| R | 20 | Gr4.1 | 82 | ATGCACCACTGATTTGGTGA | 83 | TTCACAACCAGTGACCACAA |
| S | 21 | Gr4.2 | 84 | TAGCTGCTACCACGCACACT | 85 | GGCCTTGTACGTTGTTGGAC |
| T | 22 | Gr4.3 | 86 | TTTTATGCCCACACCTCCAT | 87 | GTGTGGCGTACTTCAGACCA |
| U | 23 | Gr4.4 | 88 | ATCTGTATGGGAACCGTGCT | 89 | TGTCTTGGAGGGGTGGTTAG |
| V | 24 | Gr4.5 | 90 | TGCACGTTGCTTCCTTTGTA | 91 | AGAGTGCTCGGTCACTCACA |
| W | 25 | Gr4.6 | 92 | TTTGGGCTCCACATGTCATA | 93 | GTACGGGGATGTTTTGGTTG |
| X | 26 | Gr4.7 | 94 | GGTGATTAGCCCGTTTTTCA | 95 | ATAAGATGCGCCCATAGCAC |
| Y | 27 | Gr4.8 | 96 | GCACAGCCAAAGCATACAGA | 97 | AATGGGCCCACTGATAACAA |
| Z | 28 | Gr4.9 | 98 | AGCTGAGGGGAGATAGACC | 99 | AAATTCTGCCCACCAGATTG |
| AA | 29 | Gr4.10 | 100 | ACCAGCGAGAAGAGCCACTA | 101 | GTGGATGGTGAAGGAGTCGT |

TABLE 1-continued

List of primers surveyed

| Primer Set | Target SEQ ID | Target Name | Left (Forward) Primer SEQ ID | Left (Forward) Primer Sequence | Right (Reverse) Primer SEQ ID | Right (Reverse) Primer Sequence |
|---|---|---|---|---|---|---|
| AB | 30 | Gr4.11 | 102 | CCTCGCACTTGTGCTCATTA | 103 | TGTGCAATGAAGCCATGTTT |
| AC | 31 | Gr4.12 | 104 | TCCCTGTGACACTGCAAGAG | 105 | CCCCGGACTTCAACAGTCTA |
| AD | 32 | Gr4.13 | 106 | TGACAGCCACTCGAGAACAG | 107 | GCCAACAATCACAGCAATGT |
| AE | 33 | Gr4.14 | 108 | ACAGGGTGACTGGAATGGAG | 109 | AGGCATTCTGGTGTCTGTCC |
| AF | 34 | Gr4.15 | 110 | GATCAAGGGGAGATCGTCAA | 111 | CCGATGCCTTGAAAATGACT |
| AG | 35 | Gr4.16 | 112 | CTGACACATGTCCTGGTTGG | 113 | ATGGCATCAAGATCCTCTGG |
| AH | 36 | Gr4.17 | 114 | ATTTTGCGCATGGATATGGT | 115 | GACGGTGAGGCCTGTTATGT |
| AI | 37 | Gr4.18 | 116 | GAAGTTTTCCGCCTTCCTCT | 117 | TTGCCAAACTGCTTCACAAG |
| AJ | 38 | Gr4.19 | 118 | CTGTCACCGGAGAAGAGGAG | 119 | GGAGGTCGAAGAGAGTGACG |
| AK | 38 | Gr4.19 | 120 | CTCGACAGGGGAGTTCTCAG | 121 | CGGCCAACTCATTATCTCGT |
| AL | 40 | Gr4.21 | 122 | GCACGAGGCTAACACAAACA | 123 | GACAACATTCTCCGCTTGGT |
| AM | 41 | pRC | 124 | TTGTTCATCAAGGCAGCAAG | 125 | CGCAGTCGACATGGTTTATG |
| AN | 42 | pSHR | 126 | CTTAATTGGCAGGGTGCAGT | 127 | GACATCTACAACGCCGTCCT |
| AO | 43 | Rhiz1-12 | 128 | ATAAGTTGGCATTGGCTTCG | 129 | CAGCGAACTCAACAATGCAC |
| AP | 44 | Rhiz1-27 | 130 | CTCGTGTTGTTGCTCGTGTT | 131 | CGGAGAATAGCTCCATTCCA |
| AQ | 45 | Rhiz1-36 | 132 | GTGGAGTGGGTCCTCAAGAA | 133 | GTATCACACACGCCCACTTG |
| AR | 46 | Rhiz1-5 | 134 | CCCTCAAGACCCTGTTGTGT | 135 | GTTGTAAAGCCAGGCCACAT |

*Sorghum* and Johnsongrass Samples:

Following primer design, the 44 primer sets listed in Table 1 were used in validation experiments against multiple samples of sorghum and Johnsongrass. The samples tested included 36 sorghum samples from Pioneer Hi-Bred's germplasm and 18 Johnsongrass extensions, four of which were collected from Pioneer Hi-Bred's fields in Texas (designated JG1-4) and the remainder originating from a variety of other geographical locations were provided by John Erpelding of the USDA-ARS, Tropical Agriculture Research Station in Puerto Rico. Table 2 lists the samples of various sorghum varieties and Johnsongrass extensions that were used in this study.

TABLE 2

Samples of sorghum and Johnsongrass surveyed

| Sorghum | Johnsongrass | source |
|---|---|---|
| PHY50FW leaf | EDH7 | JG1 Plainview, TX |
| PHY50FW SS | FPA66 | JG2 Plainview, TX |
| PHY50FW bulkf | NTC31 | JG3 Plainview, TX |
| ShumSS F1 | ZYL24 | JG4 Plainview, TX |
| ShumSS F2 | 8M429W | Grif14527 (USDA) |
| ShumSS F3 | CAJ14W | Grif14530 (USDA) |
| ABH23G | ENZ27W | Grif14531 (USDA) |
| AGK1G | FEH14W | Grif16339 (USDA) |

TABLE 2-continued

Samples of sorghum and Johnsongrass surveyed

| Sorghum | Johnsongrass | | source |
|---|---|---|---|
| HVC2G | IC0010W | PI185458 | (USDA) |
| KCK8G | IFU870W | PI201766 | (USDA) |
| MPH30G | IPU970W | PI209217 | (USDA) |
| QL35G | IZY39W | PI228364 | (USDA) |
| QTA51G | MEY16W | PI271615 | (USDA) |
| EC78GW | YGC87W | PI302160 | (USDA) |
| YGY5GW | IS3620C | PI302268 | (USDA) |
| BTX623 | MFY55W | PI302277 | (USDA) |
| SS6B@ | P9990GW | PI302281 | (USDA) |
| YYJ6G | YYU28W | Sorghum halepense | Puerto Rico (USDA) |

Sample Preparation:

*Sorghum* samples were received in the form of genomic DNA from Pioneer Hi-Bred Research Center in Georgetown, Canada. The sorghum DNAs were isolated from 2 cm×2 cm (for fully developed plants) or 3 cm×3 cm (for young plants) pieces of leaf tissue as follows: The tissues were freeze dried overnight and then ground by placing stainless steel balls in the sample tube and shaking the tube in a paint shaker for 90 seconds. 250 µl of the dried, ground tissue was taken to a new tube and combined with 900 µl of extraction buffer containing 2% hexadecyltrimethyl ammonium bromide, 1.4M NaCl, 100 mM Tris-Cl pH 8.0, 20 mM EDTA, 0.5% sodium bisulfate and 1% β-mercaptoethanol. The samples were incubated at 65° C. for 40 minutes and then the DNA was isolated via a standard extraction method utilizing chloroform/isoamyl alcohol (24:1 v:v), isopropanol, and centrifugation. The DNA was washed in 70% ethanol, dried, and then resuspended in water containing 50 μg/ml RNase.

Johnsongrass varieties were received as seed. To prepare leaf DNA samples, seeds were grown in flats in a growth room until plants were mature enough for the leaves to be sampled. Leaves were sampled by cutting vegetative tissue equivalent to approximately eight leaf punches (1-2 inch long leaf strips). Leaf samples were frozen and then lyophilized over night in a freeze-drier. Dry tissue was ground to powder on a Genogrinder at 1500 strokes/min for one minute prior to DNA isolation. DNA isolation was performed using a NucleoSpin DNA isolation kit (Macherey-Nagel) following the manufacturer's recommended protocol. To prepare seed DNA samples, seed was ground into flour and then DNA was isolated from that material using a NucleoSpin DNA isolation kit (Macherey-Nagel) following the manufacturer's recommended protocol.

PCR reactions. PCR amplifications were performed on Mx3000 and Mx3005 (Stratagene) thermocyclers. Reactions were set up using 50 ng Genomic DNA, 4 μM of each primer, Stratagene 2X Brilliant master mix and 0.4 μl ROX reference dye in a total reaction volume of 25 μl. The theromocycle profile included an enzyme activation step at 95° C. for 10 minutes; 40 cycles of denaturation at 95° C. for 30 sec, annealing at 60° C. for 60 sec, elongation at 72° C. for 30 sec and a post-cycling final elongation at 72° C. for 7 min. In each run, for every genomic DNA sample used, there was also an endogenic gene control, Sorgoleone 1 (SOR1, Yang, et al., 2004) amplification performed to ensure the amplicability of the DNA. Positive amplification was determined using SYBR Green melt curve analysis as well as visualization via 2% agarose gel electrophoresis. The results of this screen are shown in Table 3, below. Primer sets that gave positive amplification results from Johnsongrass DNA but not from sorghum DNA were subsequently used in a second round of screening.

TABLE 3

Results of first round screening of potential Johnsongrass detection sequences

| Primer set | SEQ ID | Target Name | Sorghum PHY50FW | Johnsongrass JG1 Leaf | Johnsongrass JG1 Seed | Johnsongrass JG4 Leaf |
|---|---|---|---|---|---|---|
| A | 1 | Contig7 | Y | Y | | |
| B | 2 | Contig39 | Y | Y | | |
| C | 3 | Contig44 | Y | Y | | |
| D | 4 | Contig46 | Y | Y | | |
| E | 5 | Contig51 | Y | Y | | |
| F | 6 | Gr2.1 | N | | N | |
| G | 9 | Gr2.4 | N | | N | |
| H | 10 | Gr2.5 | N | | N | |
| I | 11 | Gr2.6 | Y | | Y | |
| J | 12 | Gr2.7 | N | | N | |
| K | 13 | Gr2.8 | N | | N | |
| L | 14 | Gr2.9 | Y | | Y | |
| M | 15 | Gr2.10 | N | | N | |
| N | 16 | Gr2.11 | N | | Y | |
| O | 17 | Gr2.12 | N | | Y | |
| P | 18 | Gr2.13 | N | | Y | |
| Q | 19 | Gr2.14 | Y/N | | Y | |
| R | 20 | Gr4.1 | Y | | Y | |
| S | 21 | Gr4.2 | N | | Y | |
| T | 22 | Gr4.3 | Y | | Y | |
| U | 23 | Gr4.4 | Y | | Y | |
| V | 24 | Gr4.5 | Y | | Y | |
| W | 25 | Gr4.6 | Y | | Y | Y |
| X | 26 | Gr4.7 | N | | N | |
| Y | 27 | Gr4.8 | Y | | Y | |
| Z | 28 | Gr4.9 | Y | | Y | Y |
| AA | 29 | Gr4.10 | Y | | Y | Y |
| AB | 30 | Gr4.11 | N | | Y | Y |
| AC | 31 | Gr4.12 | N | | Y | |
| AD | 32 | Gr4.13 | Y | | Y | Y |
| AE | 33 | Gr4.14 | Y | | Y | Y |
| AF | 34 | Gr4.15 | Y | | Y | Y |
| AG | 35 | Gr4.16 | Y | | Y | Y |
| AH | 36 | Gr4.17 | N | | Y | Y |
| AI | 37 | Gr4.18 | N | | Y | Y |
| AJ | 38 | Gr4.19 | N | | Y | N |
| AK | 38 | Gr4.19 | Y | | Y | Y |
| AL | 40 | Gr4.21 | N | | N | N |
| AM | 41 | pRC | Y | Y | | |
| AN | 42 | pSHR | Y | Y | | |
| AO | 43 | Rhiz1-12 | Y | Y | | |
| AP | 44 | Rhiz1-27 | Y | Y | | |
| AQ | 45 | Rhiz1-36 | Y | Y | | |

PCR Screening:

Each of the 44 primer sets was initially screened against sorghum PHY50FW and one or two of three different possible Johnsongrass samples (JG1 leaf, JG1 seed, and JG4 leaf). Genomic DNA of the samples was used as template in In the second part of the survey, nine primer sets were selected for screening across all of the 54 sorghum and Johnsongrass samples. The primer sets selected were primer sets N, O, P, S, AB, AC, AH, AI and AJ, which are directed toward Johnsongrass detection sequences Gr2.11, Gr2.12, Gr2.13, Gr4.2, Gr4.11, Gr4.12, Gr4.17, Gr4.18 and Gr4.19, respectively. PCR amplifications were performed as described above and positive amplification results were again determined using SYBR Green melt curve analysis as well as visualization via 2% agarose gel electrophoresis. The results of this screen are shown in Table 4, below.

TABLE 4

Results of screen of nine select primer sets against 54 samples of Johnsongrass and sorghum

| Sorghum or Johnsongrass sample | Primer set N (Gr2.11) | Primer set O (Gr2.12) | Primer set P (Gr2.13) | Primer set S (Gr4.2) | Primer set AB (Gr4.11) | Primer set AC (Gr4.12) | Primer set AH (Gr4.17) | Primer set AI (Gr4.18) | Primer set AJ (Gr4.19) |
|---|---|---|---|---|---|---|---|---|---|
| JG1 | + | + | + | + | + | + | + | + | +/− |
| JG2 | + | + | + | + | + | + | + | + | + |
| JG3 | − | + | − | + | − | + | + | + | − |
| JG4 | + | + | + | + | + | − | + | + | − |
| Grif14527 | + | + | + | + | + | + | + | + | + |
| Grif14530 | − | + | − | + | +/− | + | + | + | +/− |
| Grif14531 | + | + | + | + | + | + | + | + | − |
| Grif16339 | − | + | + | + | + | + | + | + | − |
| PI185458 | − | + | + | + | + | + | + | + | − |
| PI201766 | + | + | + | + | +/− | + | + | + | − |
| PI209217 | + | + | − | + | + | + | + | + | − |
| PI228364 | + | + | − | + | +/− | + | + | +/− | +/− |
| PI271615 | − | + | + | + | + | + | + | + | + |
| PI302160 | + | + | + | + | − | + | + | + | + |
| PI302268 | + | + | − | + | + | + | + | + | + |
| PI302277 | + | + | + | +/− | − | + | − | + | − |
| PI302281 | + | + | + | + | +/− | + | − | + | − |
| *S. halepense* | + | + | + | + | + | + | + | + | + |
| PHY50FWleaf | − | − | − | − | − | − | − | − | − |
| PHY50FWSS | − | − | − | − | − | − | − | − | − |
| PHY50FWbulkf | − | − | − | +/− | − | − | − | − | − |
| ShumSS F1 | − | − | − | − | − | − | − | − | − |
| ShumSS F2 | − | +/− | − | − | − | − | − | − | − |
| ShumSS F3 | − | − | − | − | − | − | − | − | − |
| ABH23G | − | − | − | − | − | − | − | +/− | − |
| AGK1G | − | − | − | +/− | − | − | − | − | − |
| HVC2G | − | − | − | − | − | − | − | − | − |
| KCK8G | − | − | − | +/− | − | − | − | − | − |
| MPH30G | − | − | − | − | − | − | − | − | − |
| QL35G | − | − | + | − | − | − | − | − | − |
| QTA51G | − | − | − | +/− | − | − | − | − | − |
| EC78GW | − | +/− | − | +/− | − | − | − | +/− | − |
| YGY5GW | − | − | − | − | − | − | − | − | − |
| BTX623 | − | − | − | − | − | − | − | − | − |
| SS6B@ | − | − | − | − | − | − | − | − | − |
| YYJ6G | − | − | − | − | − | − | − | − | − |
| EDH7 | − | − | + | − | − | − | +/− | − | − |
| FPA66 | − | − | − | − | − | − | − | − | − |
| NTC31 | − | − | − | − | − | − | − | − | − |
| ZYL24 | − | − | + | − | − | − | − | − | − |
| 8M429W | − | − | − | − | − | − | − | − | − |
| CAJ14W | − | − | − | +/− | − | − | − | +/− | − |
| ENZ27W | − | − | +/− | − | − | − | − | − | − |
| FEH14W | − | − | − | − | − | − | − | − | − |
| IC0010W | − | − | + | − | − | − | − | +/− | − |
| IFU870W | − | − | + | +/− | − | − | − | − | − |
| IPU970W | − | − | + | − | − | − | − | − | − |
| IZY39W | − | − | +/− | − | − | − | − | − | − |
| MEY16W | − | − | − | − | − | − | − | +/− | − |
| YGC87W | − | − | + | − | − | − | − | − | − |
| IS3620C | − | − | − | − | − | − | − | − | − |
| MFY55W | − | − | − | − | − | − | − | − | − |
| P9990GW | − | − | − | +/− | − | − | − | − | − |
| YYU28W | − | − | + | +/− | − | − | − | − | − |

Example 3

Real-Time PCR Trial

Probe Design:

Five of the Johnsongrass detection sequences identified through the in silico analysis of Example 1 and tested through the PCR screening of Example 2 were selected for Taqman® Real-Time PCR probe design. The Primer3 software program was again used to design the Taqman® probes using the default software settings. Each probe was designed with a FAM reporter attached to its 5' end and a BHQ1 quencher attached to its 3' end. Table 5 lists the five probe sequences that were designed.

TABLE 5

Probes directed toward specific Johnsongrass detection sequences

| Probe SEQ ID NO. | Target SEQ ID NO. | Name | Probe Sequence |
|---|---|---|---|
| 136 | 17 | Gr2.12 | Fam-CAAGACATCCAGCGTTTCCT-BHQ1 |
| 137 | 21 | Gr4.2 | Fam-GATCGATCGATCGAGCAAGT-BHQ1 |
| 138 | 31 | Gr4.12 | Fam-TCTCAAAGGGAAAACGATGG-BHQ1 |
| 139 | 36 | Gr4.17 | Fam-CATACTGCGAGCAGACCAAC-BHQ1 |
| 140 | 37 | Gr4.18 | Fam-TGTTTAGGCGAAGGGAAATG-BHQ1 |

Real-Time PCR:

To test the ability of a real-time PCR technique to detect Johnsongrass DNA in a background of sorghum DNA, probe SEQ ID NO.: 136 with a FAM-BHQ1 reporter-quencher pair attached, which is a real-time PCR probe directed toward Johnsongrass detection sequence Gr2.12 (SEQ ID NO.: 17), was used in conjunction with the above-discussed primers directed toward that same Johnsongrass detection sequence (Primer set O) in a real-time PCR trial. Each reaction performed contained 50-100 ng genomic DNA, 9 µM of each primer from primer set O, 4 µM of the SEQ ID NO.: 136 probe and Roche master mix in a total reaction volume of 25 µl. Further, each reaction was a multiplex reaction including primers (4 µM each of forward and reverse) and a probe (4 µM) directed toward a Johnsongrass/sorghum positive endogenic control gene, ADHexon4_3, to ensure the amplification was working properly. The amplifications were performed on Mx3000 and Mx3005 (Stratagene) thermocyclers using a theromocycle profile that included an enzyme activation step at 95° C. for 10 minutes followed by 40 cycles of denaturation at 95° C. for 10 sec, annealing at 60° C. for 60 sec and elongation at 72° C. for 30 sec.

The genomic DNA employed in each PCR reaction was sorghum YS8400 genomic DNA with varying amounts of Johnsongrass JG1 DNA spiked therein, the ratios of Johnsongrass JG1:sorghum YS8400 DNA ranging from 1:1000 to 1:10,000. In addition, pure sorghum YS8400 DNA and pure Johnsongrass JG1 DNA were used in negative and positive control reactions, respectively. In total 12 separate reaction mixtures were tested, each one being carried out either in triplicate or sextuplicate. The results of this study can be found in Table 6.

TABLE 6

Real-time PCR trial of Johnsongrass detection sequence Gr.2.12 (SEQ ID No.: 17)

| | Test Mixture | | | | | | | | | | | |
|---|---|---|---|---|---|---|---|---|---|---|---|---|
| | S1 | S2 | S3 | S4 | S5 | S6 | S7 | S8 | S9 | S10 | S11 | S12/S13 |
| | \multicolumn{10}{c}{JG1:Sorghum DNA Ratio} | Pure Sorghum | Pure Johnsongrass |
| | 1:1000 | 1:2000 | 1:3000 | 1:4000 | 1:5000 | 1:6000 | 1:7000 | 1:8000 | 1:9000 | 1:10,000 | | |
| Rep. 1 | + | + | + | + | + | + | + | − | + | + | − | + |
| Rep. 2 | + | + | + | + | − | + | + | + | + | + | − | + |
| Rep. 3 | + | + | + | + | + | + | + | − | + | − | − | + |
| Rep. 4 | + | + | + | | | | | | | | | + |
| Rep. 5 | + | + | + | | | | | | | | | + |
| Rep. 6 | + | + | + | | | | | | | | | + |

As these results indicate, using the Gr2.12 (SEQ ID NO.: 17) Johnsongrass detection sequence, in this example, the real-time PCR method is able to successfully detect Johnsongrass DNA in a background of sorghum DNA, even at a 1:10,000 ratio.

Example 4

Seed Lot Testing

Tests were also performed to determine the ability of real-time PCR analysis of Johnsongrass detection sequences to detect Johnsongrass contamination in a sorghum seed lot. Three separate sorghum seed lots were tested: 84G62-2101, 84G62-N284 and 85G47-M042. For each of the three seed lots, 20 jars of seeds, each jar containing 6,000 seeds, were examined by real time PCR. For each jar, the seeds were first ground to flour and then the DNA from the seed flour was isolated using a NucleoSpin DNA isolation kit (Macherey-Nagel) as per the manufacturer's recommended protocol. The real-time PCR reactions were performed as described in Example 3 above, again using the probe (SEQ ID NO.: 136) directed toward Johnsongrass detection sequence Gr2.12 (SEQ ID NO.: 17). Further, in addition to the experimental samples, a negative control reaction (pure sorghum YS8400 flour) and several positive control reactions (pure Johnsongrass JG3 seed pools; spiked Johnsongrass seed into a sorghum seed jar at a 1:6000 ratio; and spiked Johnsongrass DNA into a sorghum DNA sample at a 1:3000 ratio) were performed.

In this experimental trial, the real time PCR technique was able to positively identify Johnsongrass contamination (positive Johnsongrass amplification) in two of the 20 jars tested for sorghum lot number 84G62-N284, while the other two sorghum lots tested were found to be negative. This shows the potential usefulness of this method and the identified Johnsongrass detection sequences for detecting Johnsongrass contamination in sorghum seed lots.

The present disclosure is not limited to the embodiments described and exemplified above, but is capable of variation and modification within the scope of the appended claims.

What is claimed is:

1. A method of determining quality of *Sorghum bicolor* seed production, the method comprising:
   a. providing a biological sample comprising *Sorghum bicolor* seeds, wherein the biological sample is suspected of also containing Johnsongrass or Johnsongrass hybrid genetic material;
   b. providing the primer pair of SEQ ID NOS.: 76 and 77 or the probe of SEQ ID NO: 136 that selectively binds to the Johnsongrass or Johnsongrass hybrid genetic material to discriminate against related genetic material;
   c. performing a hybridization or an amplification reaction wherein the primer pair of SEQ ID NOS.: 76 and 77 or probe of SEQ ID NO: 136 binds to Johnsongrass or Johnsongrass hybrid genetic material and does not substantially bind to genetic material from *Sorghum bicolor*; and
   d. determining the quality of *Sorghum bicolor* seed production based on the presence or the amount of Johnsongrass or Johnsongrass hybrid genetic material.

2. The method of claim 1, wherein the genetic material is DNA.

* * * * *